(12) United States Patent
Rajaraman et al.

(10) Patent No.: US 11,746,320 B2
(45) Date of Patent: Sep. 5, 2023

(54) METHOD OF FORMING HIGH-THROUGHPUT 3D PRINTED MICROELECTRODE ARRAY

(71) Applicant: UNIVERSITY OF CENTRAL FLORIDA RESEARCH FOUNDATION, INC., Orlando, FL (US)

(72) Inventors: Swaminathan Rajaraman, Winter Park, FL (US); Avra Kundu, Orlando, FL (US); Adam Rozman, Oviedo, FL (US); Jorge Manrique Castro, Orlando, FL (US)

(73) Assignee: UNIVERSITY OF CENTRAL FLORIDA RESEARCH FOUNDATION, INC., Orlando, FL (US)

(*) Notice: Subject to any disclaimer, the term of this patent is extended or adjusted under 35 U.S.C. 154(b) by 101 days.

(21) Appl. No.: 17/348,866

(22) Filed: Jun. 16, 2021

(65) Prior Publication Data

US 2021/0394434 A1 Dec. 23, 2021

Related U.S. Application Data

(60) Provisional application No. 63/042,200, filed on Jun. 22, 2020.

(51) Int. Cl.
*B29C 64/124* (2017.01)
*C12M 1/34* (2006.01)
(Continued)

(52) U.S. Cl.
CPC ........... *C12M 41/46* (2013.01); *B29C 64/124* (2017.08); *B33Y 10/00* (2014.12); *B33Y 80/00* (2014.12);
(Continued)

(58) Field of Classification Search
CPC ...... C12M 41/46; C12M 23/12; C12M 23/16; C12M 23/22; C12M 25/08; C12M 25/02;
(Continued)

(56) References Cited

U.S. PATENT DOCUMENTS

| 9,279,801 B2 | 3/2016 | Rajaraman et al. |
| 2015/0027885 A1* | 1/2015 | Rajaraman ......... G01N 33/4836 |
| | | 204/403.13 |

(Continued)

FOREIGN PATENT DOCUMENTS

WO    WO-2020051366 A1 *    3/2020    ............ A61B 5/291

OTHER PUBLICATIONS

Kundu et al., "3D Printing, Ink Casting and Micromachined Lamination (3D PICLM): A Makerspace Approach to the Fabrication of Biological Microdevices", Micromachines 2018,9,85, Published Feb. 15, 2018. (Year: 2018).*

(Continued)

*Primary Examiner* — Joseph S Del Sole
*Assistant Examiner* — Lawrence D. Hohenbrink, Jr.
(74) *Attorney, Agent, or Firm* — Allen, Dyer, Doppelt + Gilchrist, P.A.

(57) ABSTRACT

A method of forming a high-throughput, three-dimensional (3D) microelectrode array for in vitro electrophysiological applications includes 3D printing a well plate having a top face and bottom face. A plurality of culture well each includes a plurality of 3D printed, vertical microchannels and microtroughs communicating with the microchannels.

(Continued)

The microtroughs and the microchannels are filled with a conductive paste to form self-isolated microelectrodes in each of the culture wells and conductive traces that communicate with the self-isolated microelectrodes.

24 Claims, 24 Drawing Sheets

(51) Int. Cl.
| | |
|---|---|
| *C12M 1/00* | (2006.01) |
| *C12M 1/32* | (2006.01) |
| *B33Y 10/00* | (2015.01) |
| *B33Y 80/00* | (2015.01) |
| *C12M 3/06* | (2006.01) |
| *C12M 1/12* | (2006.01) |
| *C12M 1/42* | (2006.01) |
| *G01N 33/483* | (2006.01) |
| *G01N 35/00* | (2006.01) |
| *C12M 1/26* | (2006.01) |

(52) U.S. Cl.
CPC ............ *C12M 23/12* (2013.01); *C12M 23/16* (2013.01); *C12M 23/22* (2013.01); *C12M 25/08* (2013.01); *C12M 35/02* (2013.01); *C12M 33/00* (2013.01); *G01N 33/4836* (2013.01); *G01N 2035/00158* (2013.01)

(58) Field of Classification Search
CPC ....... B33Y 10/00; B33Y 80/00; B29C 64/124; G01N 33/4836; G01N 2035/00158
USPC ........................................................ 264/401
See application file for complete search history.

(56) References Cited

U.S. PATENT DOCUMENTS

| | | | |
|---|---|---|---|
| 2019/0240658 A1* | 8/2019 | Rajaraman | B81B 1/006 |
| 2020/0071648 A1 | 3/2020 | Moore et al. | |
| 2021/0198613 A1* | 7/2021 | Curley | G01N 33/5014 |

OTHER PUBLICATIONS

American National Standards Institute, "ANSI Footprint Dimensions for Microplates," Society for Laboratory Automation and Screening; ANSI SLAS Jan. 2004 (R2012); Oct. 12, 2011; pp. 1-8.

Berdondini et al., "A Microelectrode Array (MEA) Integrated With Clustering Structures for Investigating in vitro Neurodynamics in Confined Interconnected Sub-Populations of Neurons," Sensors and Actuators B: Chemical vol. 114, Issue 1; Mar. 30, 2006; pp. 530-541; Abstract Only.

Koledova, "3D Cell Culture: An Introduction," Methods in Molecular Biology; 2017; 1612:1-11; Abstract Only.

Kundu et al., "3D Printing, Ink Casting and Micromachined Lamination (3D PICµM): A Makerspace Approach to the Fabrication of Biological Microdevices," Micromachines; 2018; 9, 85; pp. 1-23.

Roberts et al., "3D Printed Stainless Steel Microelectrode Arrays," 19th International Conference on Solid-State Sensors, Actuators and Microsystems (TRANSDUCERS); Jun. 2017; Abstract Only.

Skardal et al., "Organoid-on-a-Chip and Body-on-a-Chip Systems for Drug Screening and Disease Modeling," Drug Discovery Today; Sep. 2016; 21(9):1399-1411; Abstract Only.

U.S. Appl. No. 17/348,845, filed Jun. 16, 2021 Inventors: Swaminathan Rajaraman et al.

* cited by examiner

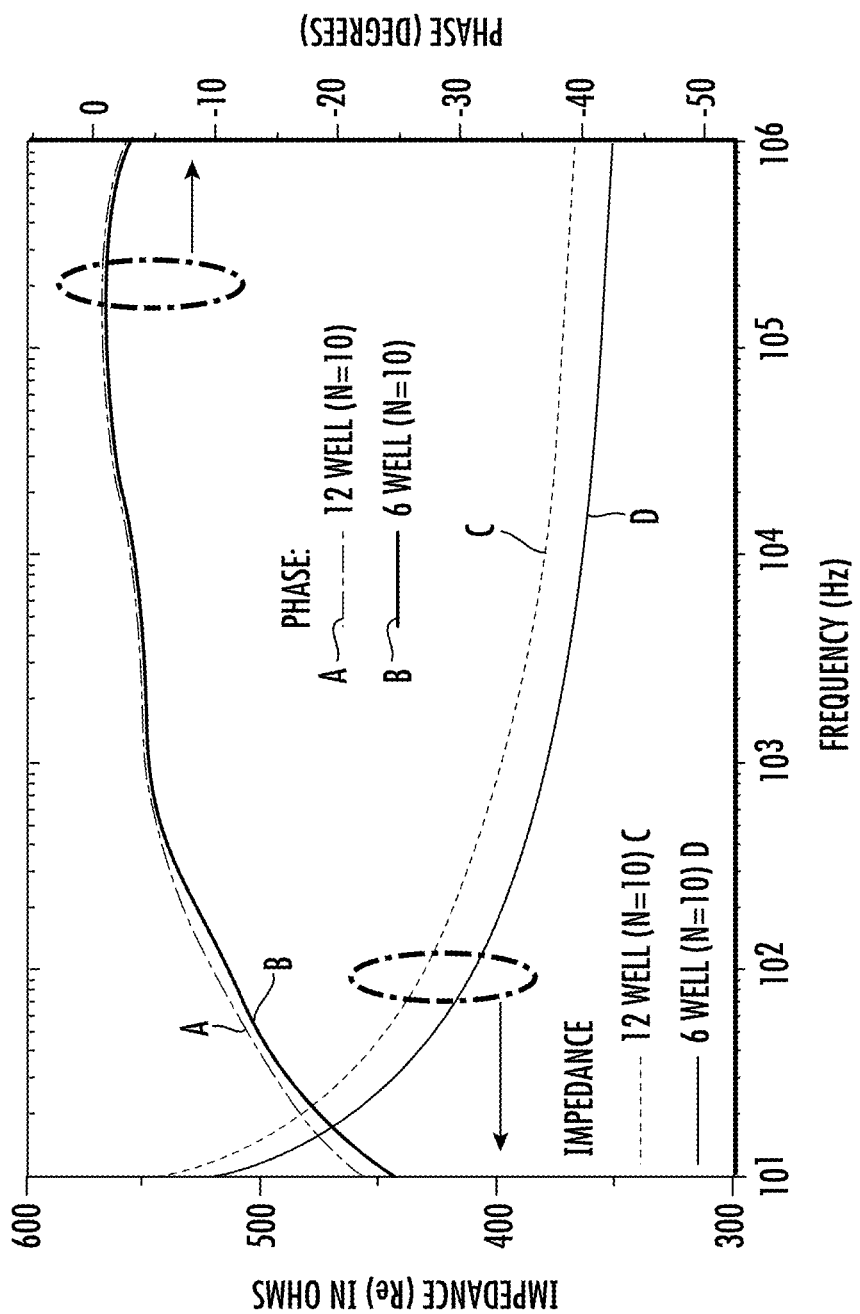

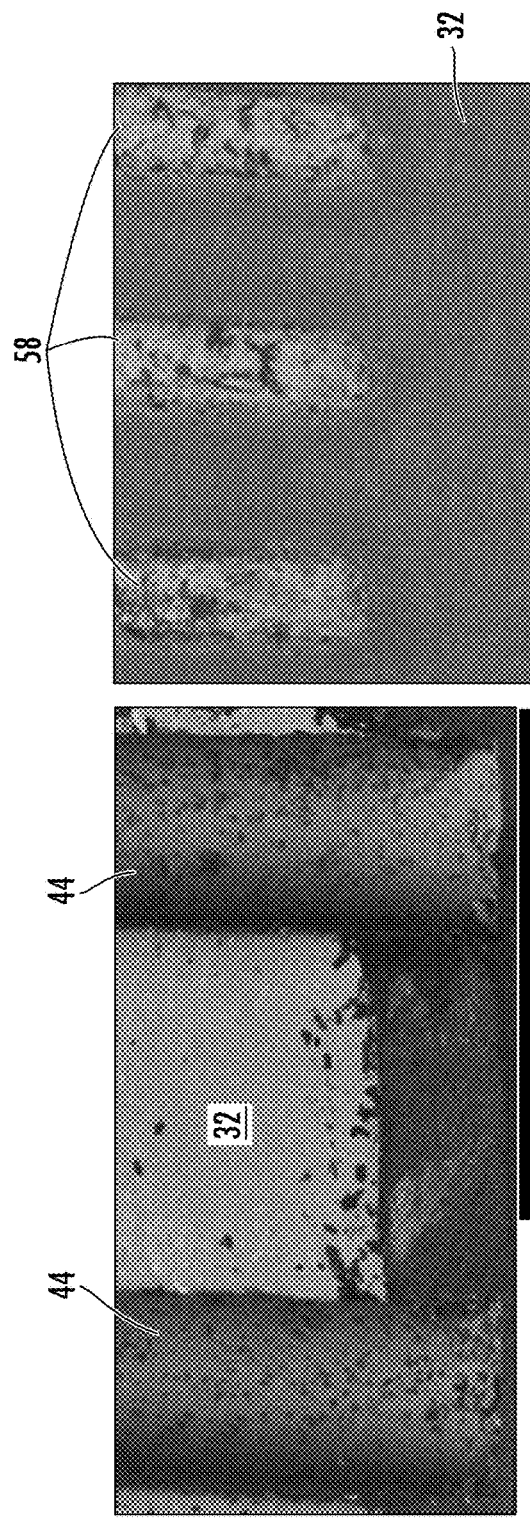
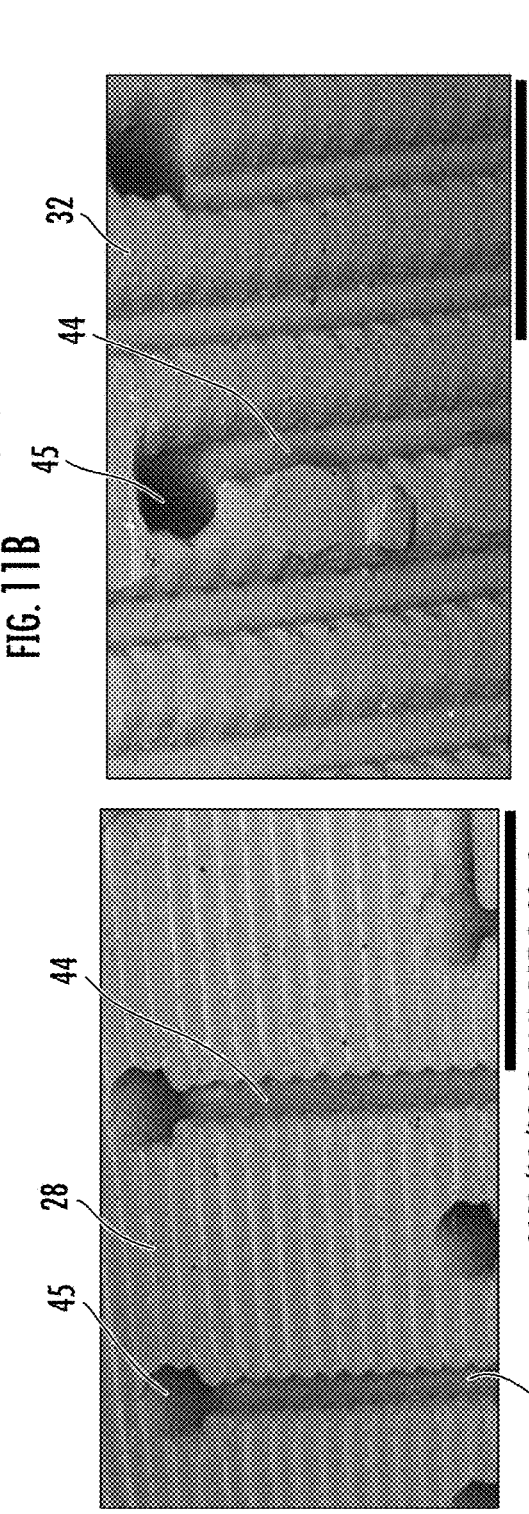
FIG. 11A
FIG. 11B
FIG. 12A
FIG. 12B

METHOD OF FORMING HIGH-THROUGHPUT 3D PRINTED MICROELECTRODE ARRAY

PRIORITY APPLICATION(S)

This application is based upon provisional application Ser. No. 63/042,200, filed Jun. 22, 2020, the disclosure which is hereby incorporated by reference in its entirety.

FIELD OF THE INVENTION

The present invention relates to high-throughput three-dimensional (3D) microelectrode arrays (MEAs) for in vitro electrophysiological applications and method of making.

BACKGROUND OF THE INVENTION

Microelectrode Arrays (MEAs) are devices that contain multiple microelectrodes through which voltage and current signals from electrically active cells are either delivered or recorded, essentially serving as interfaces that connect neurons or other electrogenic cells to electronic circuitry. There are two general classes of MEAs: 1) in vitro (outside the body) and 2) in vivo (implantable).

There has been continued work on in vitro MEAs for use in conducting electrophysiological experiments on tissue slices, spheroids, hydrogel-3D cell aggregates or dissociated cell cultures. In these experiments, the field of in vitro biology has moved rapidly toward three-dimensional (3D) models because 3D models better capture in vivo-like behavior. "Organs-on-chips," or microphysiological systems (MPSs), have been identified as the most promising candidates for these types of improved preclinical signatures. However, there are no tools currently in the market to interface electrically with these MPSs, especially in a high-throughput (HT) format. There are also relatively few tools that present 3D electrodes in a single well construction. Conventional microelectrode array platforms, including high-throughput formats that use flat 2D substrates and electrodes, are unable to capture physiologically relevant signals in three dimensions due to the low Signal to Noise Ratio (SNR) or a poor interface with the tissue-specific architecture corresponding to the 3D microphysiological systems.

In the field of conventional high-throughput biology, the standard "bio plate" is defined by the American National Standards Institute (ANSI) and Society for Lab Automation and Screening (SLAS) standards as having dimensions of about 125 mm by 85 mm (about 5-inches by about 3.34 inches). This size makes this device as a "bio plate" an awkward configuration for silicon or glass-based micro-manufacturing techniques. These types of "bio plates" contain individual culture wells that vary in number and location from 1 to 768 wells (or more) and form the microplates on which experiments are conducted. In traditional high-throughput microelectrode arrays, each of the culture wells contains planar microelectrodes, which allow for high spatial and temporal resolution of in vitro electrophysiological recordings. However, two significant challenges arise these in vitro biology applications. First, as 3D cell culturing becomes more standard to mimic in vivo-like conditions, the 2D microelectrodes positioned in the culture wells are rendered impractical and unusable. Second, the awkward geometrical shape of the "bio plate" renders standard silicon/glass wafer-based manufacturing technologies expensive, and requires multiple levels of assembly to realize a fully usable packaged device.

SUMMARY OF THE INVENTION

This summary is provided to introduce a selection of concepts that are further described below in the Detailed Description. This summary is not intended to identify key or essential features of the claimed subject matter, nor is it intended to be used as an aid in limiting the scope of the claimed subject matter.

In general, a method of forming a high-throughput, three-dimensional (3D) microelectrode array for in vitro electrophysiological applications may comprise 3D printing a well plate having a top face and bottom face and forming on the top face a plurality of culture wells, wherein each culture well includes a plurality of 3D printed, vertical microchannels on the top face, and microtroughs on the bottom face communicating with the microchannels. The method may include filling the microtroughs and the microchannels with a conductive paste to form self-isolated microelectrodes in each of the culture wells and conductive traces that communicate with the self-isolated microelectrodes.

Each microelectrode may include an enlarged top contact section. The conductive traces may terminate into contact pads configured to interface with an electrophysiological circuit component. Each culture well may include about 2 to about 64 microelectrodes. The method may comprise 3D printing a photopolymer clear resin.

The method may comprise 3D printing an outer peripheral wall extending from the top face. The microelectrodes may be arranged in an ordered or random array within each culture well.

The method may include 3D printing one or more alignment features. The method may also comprise varying a printing angle and orientation with respect to a base plane to optimize printing and isolation of the well plate, conductive traces, and microchannels.

In another example, a method of forming a high-throughput, three-dimensional (3D) microelectrode array for in vitro electrophysiological applications may comprise 3D printing a well plate having a top face and bottom face and forming on the top face a plurality of culture wells, wherein each culture well includes a plurality of 3D printed, vertical microchannels on the top face, and microtroughs on the bottom face communicating with the microchannels. The 3D printing may occur at about a zero to 90 degree print orientation tilt angle. The method may comprise ultraviolet curing the 3D printed well plate, culture wells, microchannels and microtroughs, and filling the microtroughs and microchannels with a conductive paste to form self-isolated microelectrodes in each culture well and conductive traces that communicate with the self-isolated microelectrodes. In an example, the print orientation tilt angle may be about zero degrees.

In yet another example, a method of forming a high-throughput, three-dimensional (3D) microelectrode array for in vitro electrophysiological applications may comprise forming by bottom-up 3D printing a well plate having a top face and bottom face and forming on the top face a plurality of culture wells. Each culture well may include a plurality of 3D printed, vertical microchannels on the top face, and microtroughs on the bottom face communicating with the microchannels, wherein the 3D printing occurs at about a zero to 90 degree print orientation tilt angle. The method may include ultraviolet curing the 3D printed well plate, culture wells, microchannels and microtroughs, and filling the microtroughs and the microchannels with a conductive paste to form self-isolated microelectrodes in each culture well and conductive traces that communicate with the self-isolated microelectrodes. Each of said self-isolated microelectrodes may have an electroplated top surface. The method may comprise cleaning and air drying the 3D printed well plate, culture wells, microchannels and microtroughs.

BRIEF DESCRIPTION OF THE DRAWINGS

Other objects, features and advantages of the present invention will become apparent from the Detailed Description of the invention which follows, when considered in light of the accompanying drawings in which:

FIG. 4 is a graph showing the impedance and phase for an average of ten 3D microelectrodes (N=10) in a single culture well for either a 6/12 culture well configuration.

FIGS. 11A and 11B are scanning electron microscope (SEM) images of the 0° tilt device on the conductive trace side and showing unfilled conductive traces in FIG. 11A and the ink-casted and filled conductive traces in FIG. 11B.

FIGS. 12A and 12B are SEM images of the traces side at different inclination angles with a 24° tilt device and orientation with support structures (FIG. 12A) and a 20° tilt device (FIG. 12B).

DETAILED DESCRIPTION

Figure 1A:
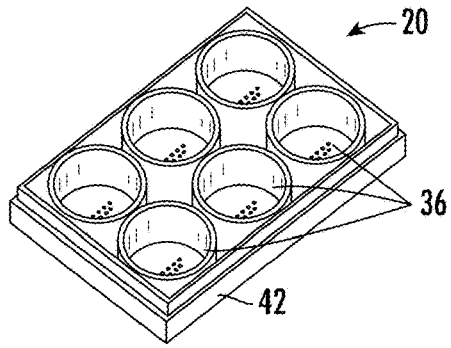
FIG. 1A is an isometric view of a 6-well 3D microelectrode array in accordance with a non-limiting example.
Figure 1B:
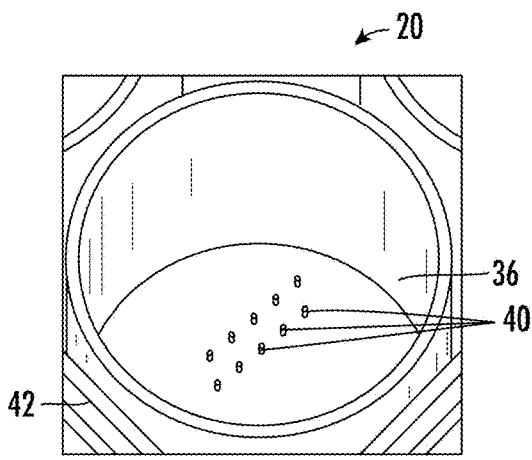
FIG. 1B is an enlarged view of a single culture well formed on the top face of the 3D printed well plate of FIG. 1A.

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

In accordance with a non-limiting example, a microfabrication process may employ 3D printing technology as described herein to produce a high-throughput (HT), self-insulated, 3D microelectrode array (MEA) that may be used for in vitro electrophysiological applications, such as electrophysiological measurements. The 3D microelectrode array has in vitro electrophysiological applications, including a lab-on-a-chip and neuropharmacological testing devices. The 3D microelectrode array may be used for cardiotoxicity assessment, disease modeling, and pre-clinical drug discovery. Because it is designed as a high-throughput device, it may be used for high-throughput phenotypic screening of drug candidates. New electrophysiological models may be developed on top of the 3D microelectrode array and be used for 3D micro-physiological system integration and evaluation and 3D organoid and spheroid integration. The 3D microelectrode array may be used in the development of new modes of sensing and integrating electrical sensing to other modes, including energy and biological sensing applications.

The 3D printing, fabrication process may incorporate micro-stereolithography (μSLA) based 3D printing technology, which not only allows for the production of 3D microelectrode geometries, but also enables the monolithic integration of all components on a "bio plate" as a 3D printed well plate that includes 3D printed standard culture wells in order to realize the high-throughput, American National Standards Institute (ANSI)/Society for Lab Automation and Screening (SLAS)-compatible geometry in 1 to 768 (or more) culture well configurations. The microelectrode array includes a bifacial configuration where the 3D printed well plate includes a top face and bottom face. The 3D microelectrodes are formed on the top face via conductive paste or ink filled microchannels in an example, that are 3D printed in each of the 3D printed culture wells. The conductive traces for electrical connections may be 3D printed on the bottom face to form the self-insulated 3D microelectrode array after metal ink casting and printing and ink filling of the 3D printed vertical microchannels. These high-throughput 3D microelectrode arrays include optical, SEM (scanning electron microscopy), Impedance Spectroscopy and well-well impedance variations, allowing a rapid, accurate, cost-effective, two step scaling-up technique to microfabricate the high-throughput 3D printed microelectrode arrays in several multi-well configurations that are compatible with standard, high-throughput assay equipment such as plate readers, robotic handlers and electrophysiological systems.

Referring now to FIGS. 1A-1I, 2A-2F, and 3A-3F, in an example, a three-dimensional (3D) microelectrode array is illustrated generally at 20 for in vitro electrophysiological applications and may be formed from a 3D printing resin, including a photopolymer clear resin. The microelectrode array 20 includes a 3D printed well plate 24 having a top face 28 and bottom face 32 (FIGS. 2A-2D and 3A-3F), and a plurality of culture wells 36 formed by 3D printing on the top face of the 3D printed well plate, and in this example, 3D printed to form what are cylindrical configured culture wells. Each culture well 36 contains an array of 3D printed hollow vertical microchannels 40 formed as cylindrical microtower structures and may be arranged in an ordered or random array within each culture well (FIGS. 1B, 1F, 3A, and 3C).

Figure 1C:
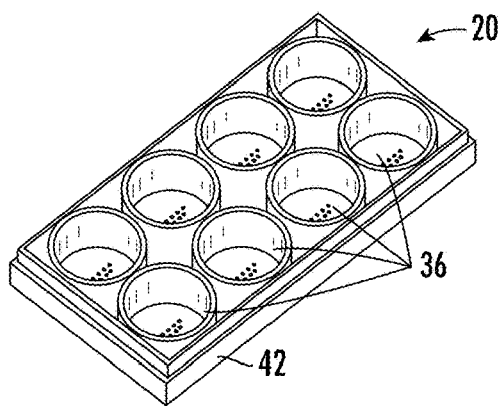
FIG. 1C is another isometric view similar to that of FIG. 1A, but showing a 12-well 3D microelectrode array.
Figure 1D:
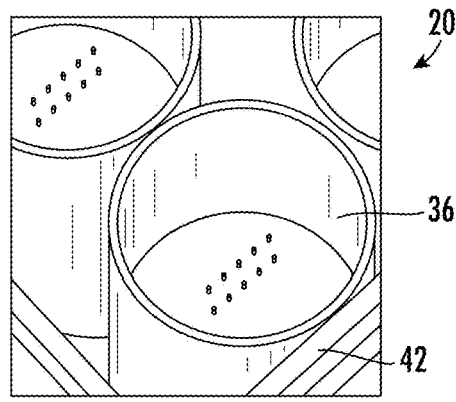
FIG. 1D is another enlarged isometric view of a single culture well on the top face of the 12-well 3D microelectrode array of FIG. 1C.
Figure 1E:
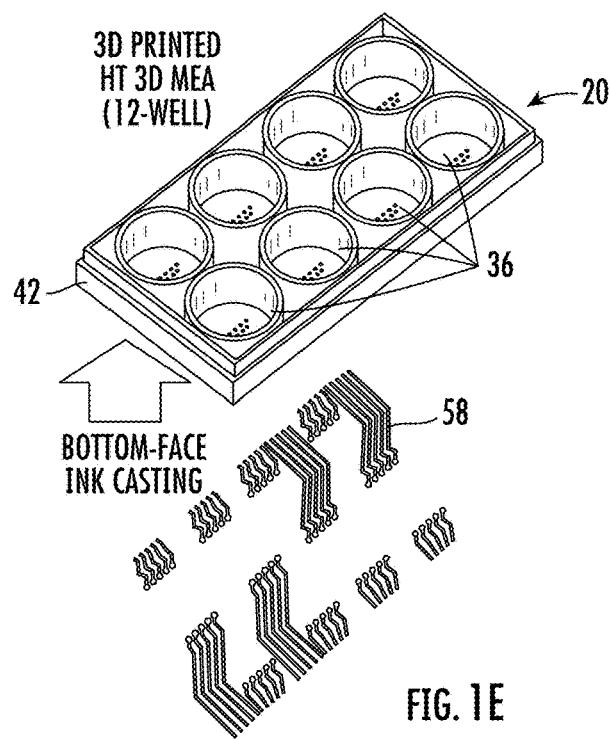
FIG. 1E is a schematic assembly view showing the silver ink casting that is applied at the bottom face opposing each culture well and connect into the microchannels that are 3D printed on the top face.
Figure 1F:
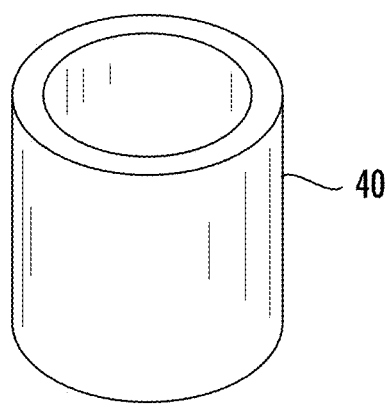
FIG. 1F is an enlarged schematic isometric view of a cylindrical microchannel formed on the top face within a cylindrical culture well.
Figure 1G:
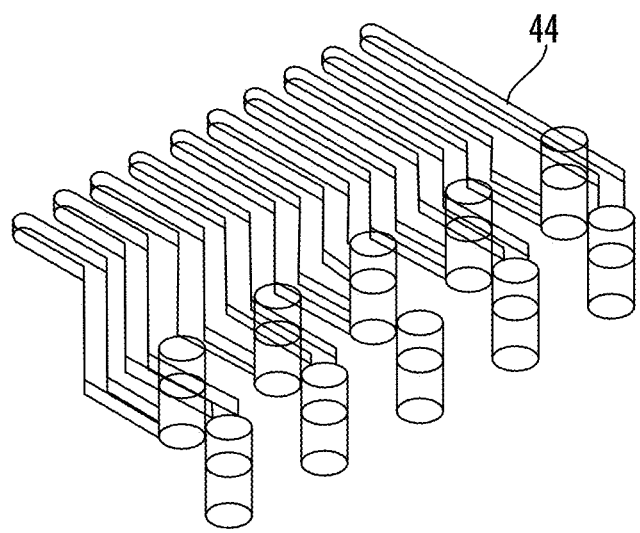
FIG. 1G is an isometric schematic view of the microtroughs and vias formed at the bottom face opposite a culture well.

The well plate 24 forming the microelectrode array 20 may have anywhere from 1 to 768 culture wells 36 also arranged in an ordered or random array, such as the illustrated example of two rows of three culture wells (6-well microelectrode array) or three rows of four culture wells (12-well microelectrode array) (FIGS. 1A, 1B, 1E, 2A-2D). A 24-well microelectrode array 20 is described in detail below with reference to FIGS. 6A-6D. The well plate 24 may include an outer peripheral wall 42 as best shown in FIGS. 1A, 1C, and 1E. Each culture well 36 includes the plurality of 3D printed hollow, vertical microchannels formed as hollow microtowers 40 on the top face 28 (FIG. 3A).

Figure 2A:
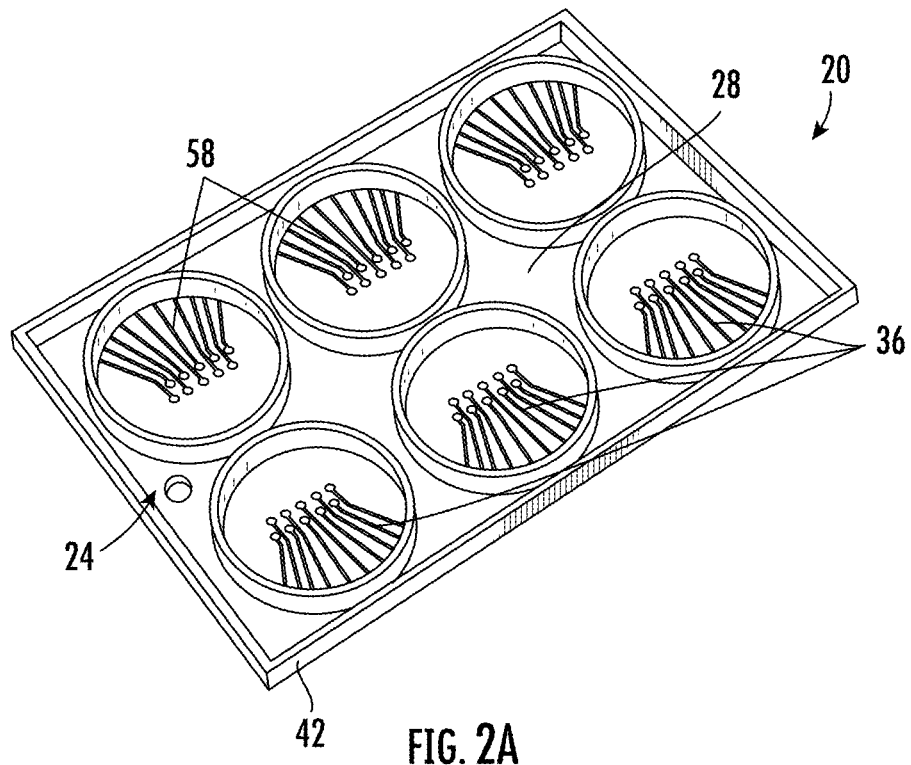
FIG. 2A is a top face isometric view of a 6-well 3D microelectrode array formed from a clear resin.
Figure 2B:
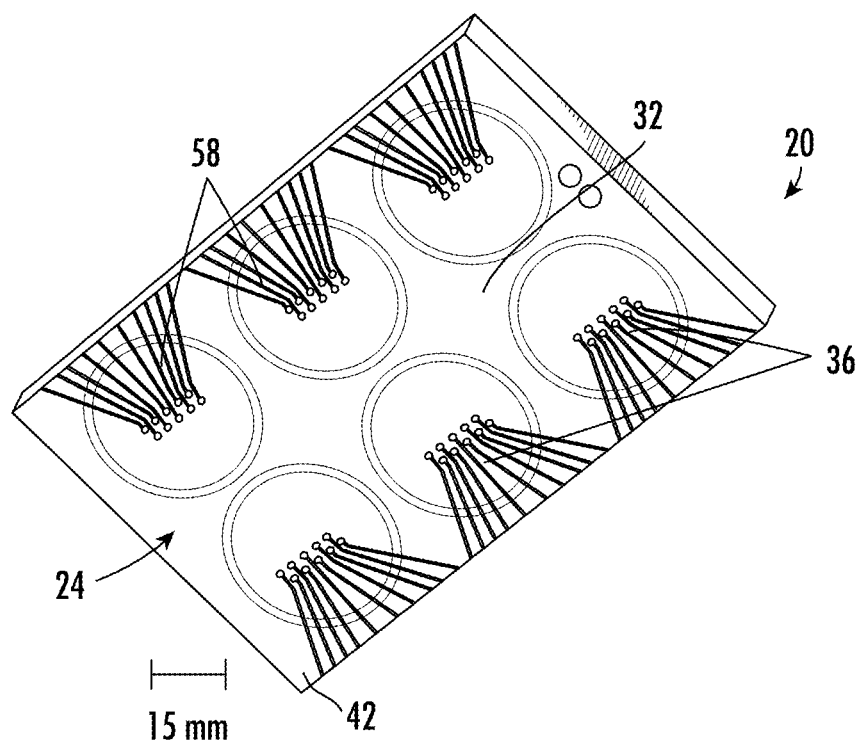
FIG. 2B is a bottom face isometric view of the 6-well 3D microelectrode array of FIG. 2A.
Figure 2C:
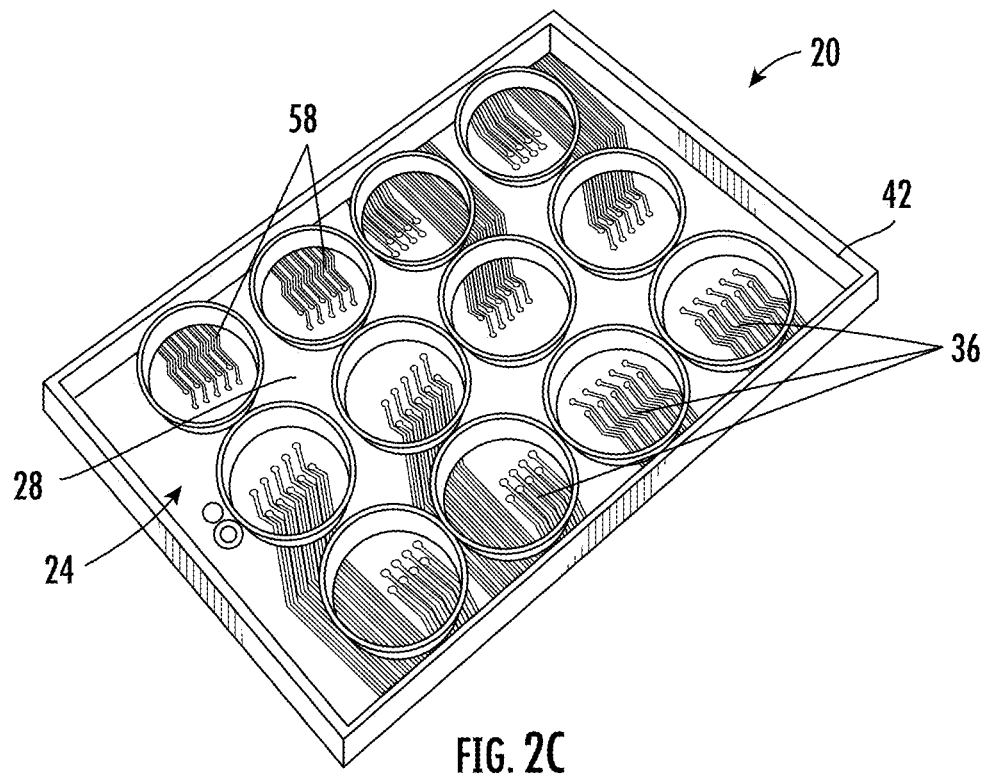
FIG. 2C is a top face isometric view of a 12-well 3D microelectrode array formed from a clear resin.
Figure 2D:
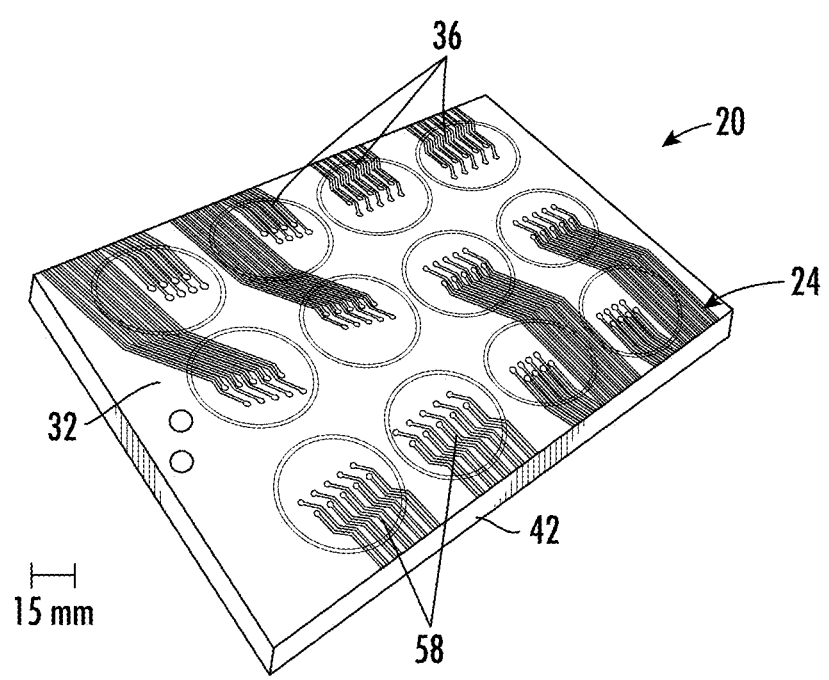
FIG. 2D is a bottom face isometric view of the 12-well 3D microelectrode array of FIG. 2C.
Figure 2E:
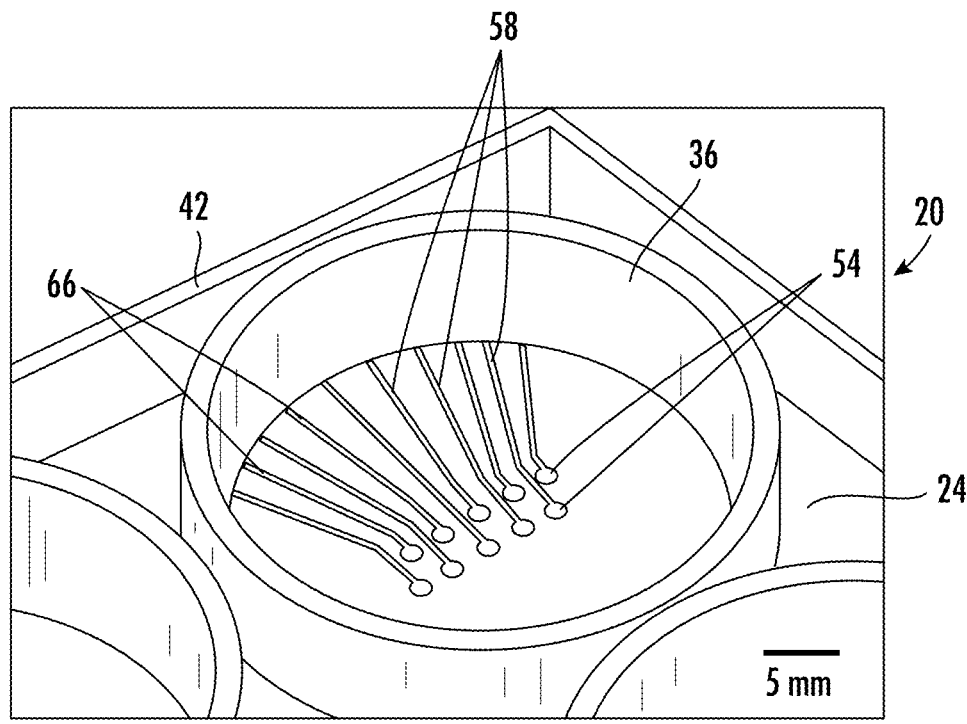
FIG. 2E is an enlarged isometric view of a single culture well in the 6-well 3D microelectrode array of FIG. 2A.
Figure 2F:
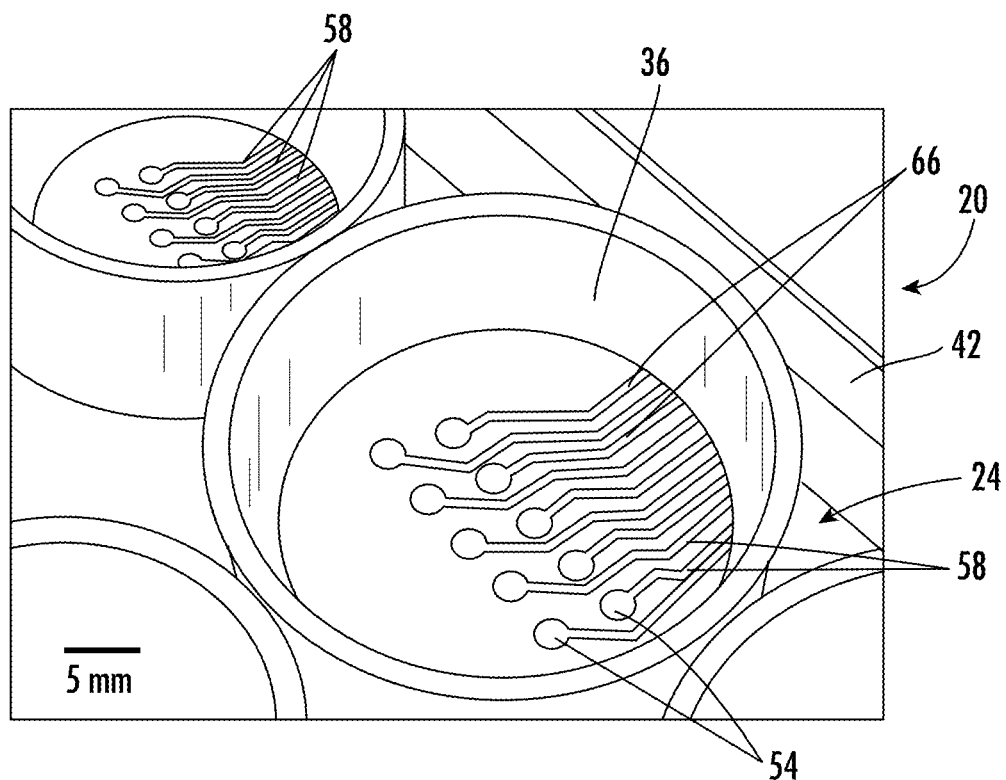
FIG. 2F is an enlarged isometric view of a single culture well in the 12-well 3D microelectrode array of FIG. 2C.
Figure 3A:
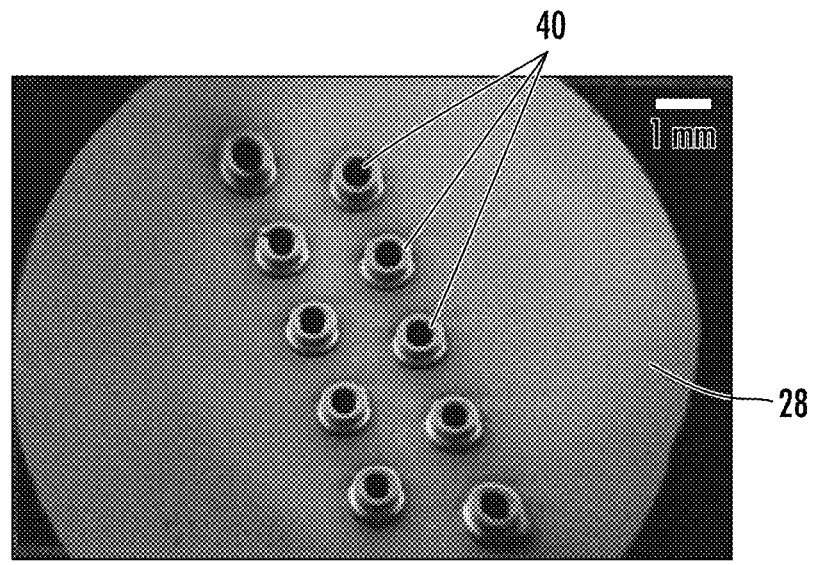
FIG. 3A is a scanning electron microscope (SEM) image of 3D printed microchannels on the top face within a culture well.

Each of the plurality of vertical microchannels 40 are also cylindrically configured and form an ordered or random array as best shown in FIG. 3A, in this example showing two rows of five vertical microchannels. Any array and number may be used, however, depending on specific requirements of the microelectrode array 20. A plurality of microtroughs 44 or small indented channel lines are formed on the bottom face 32 (FIGS. 1G, 3B, and 3D) and communicate with the vertical microchannels 40 via an orifice 45 (FIG. 3D) that communicates with the microchannel. A conductive paste 50 (FIG. 3F), which in an example, is formed as a silver ink, fills the microtroughs 44 on the bottom face 32 and the vertical microchannels as the hollow microtowers 40 on the top face 28, forming on the top face in an example an array of self-isolated microelectrodes 54 (FIGS. 1E, 1H, 2F, and 3E) in the culture wells 36, and on the bottom face, conductive traces 58 (FIGS. 1I, 2A-2D, 2E, 2F, and 3F) that communicate with the array of self-isolated microelectrodes 54, such that in this example, one conductive trace connects to one microelectrode.

In an example, each self-isolated microelectrode 54 may include an enlarged top contact section 62 (FIGS. 1H, 1I, and 3E) at the upper portion of the microchannel 40 formed from the conductive paste 50 as silver ink in an example and extends from the top face 28 in a microbullet configuration, but could be a mushroom type configuration. The conductive traces 58 may terminate into contact pads 66 (FIGS. 2E and 2F) that are configured to interface with a electrophysiological circuit component to which the 3D microelectrode array connects. Each culture well 36 may include about 5 to about 15 microelectrodes configured in an array or a non-array in a non-limiting example, yet in another example, may preferably include between about 2 and 64 microelectrodes, and in another example, up to about 1,000 microelectrodes. The 3D printed well plate 24 may be formed as a photopolymer clear resin to allow a user to see the conductive traces 58, contact pads 66, and microelectrodes 54, including the enlarged top contact sections 62 of mushroom and/or microbullet configuration, which allows integration of the 3D microelectrode array 20 with an optical microscope. Top to bottom microscopy is appropriate for the microelectrodes. Bottom-up microscopy is more difficult due to translucency of the resin and 3D structures.

A method of forming the three-dimensional microelectrode array 20 for in vitro electrophysiological applications may include 3D printing the well plate 24 having the top face 28 and bottom face 32. The method further includes 3D printing on the top face 28 the plurality of culture wells 36 formed on the top face of the 3D printed well plate 24. Each culture well includes the plurality of 3D printed, hollow, vertical microchannels 40 formed as microtowers on the top face, and further 3D printing microtroughs 44 on the bottom face 32 that communicate with the microchannels 40. The method includes filling the microtroughs 44 on the bottom face 32 and the microchannels 40 on the top face 28 with the conductive paste 50 to form on the top face the self-isolated microelectrodes 54 in each of the culture wells, and forming on the bottom face the conductive traces 58 that communicate with the self-isolated microelectrodes.

The structure as described forms a high-throughput, 3D printed microelectrode array 20. In those examples of FIGS. 1A-1I, 2A-2F, and 3A-3F, the 3D microelectrode array 20 is shown as configured and shown as either a 6-well or a 12-well microelectrode array, or as shown and described further below, the microelectrode array is shown as a 24-well bio-plate configuration that is formed using the 3D printing fabrication techniques. Example 3D printing technologies that may be used to form the 3D microelectrode array 20 include those plate and microchip systems manufactured by Axion BioSystems, MultiChannel Systems, Maxwell Biosystems, and Acea Biosciences/Agilent. Other commercially available technologies may be used, including those 3D printing systems that operate to produce planar configurations, e.g., 2D microelectrodes in some examples.

The 3D printing and similar fabrication technology that may be used to form the 3D microelectrode array 20 as illustrated and described may require only two steps in the example of 3D printing and silver ink casting/printing as shown and described to complete substantially the 3D microelectrode array. This two-step 3D printing fabrication process for the microelectrode array 20 is possible since the microelectrode array includes the unique bifacial configuration having the top face 28 and bottom face 32 that allows for two distinct advantages: 1) The array of 3D microelectrodes 54 are self-insulated and self-isolated, and 2) there is no requirement for any insulation strategy on the top face 28.

The conductive traces 58 may terminate into contact pads 66 and may extend upward into the microchannels 40 are formed on the bottom face 32, as opposed to the top face 28, which makes the integration with commercial biological/electrical amplification systems hassle-free because no through-vias are required to transition the conductive traces 58 to the bottom face 32. The fabrication components of the microelectrode array 20, such as the 3D printing resin and silver epoxy, are usually inexpensive, and the material costs to produce a 6-well, a 12-well and up to 768-well bio-plate (corresponding to the 3D printed well plate 24) for the 3D microelectrode array 20 are affordable. It is possible to configure different, arbitrary designs and conductive well changes. Rapid development of prototypes is possible for the microelectrode array 20.

The advent of additive manufacturing and microelectromechanical systems (MEMS) that are tailored to this technology are ideal to tackle the microfabrication and packaging challenges when manufacturing the microelectrode array 20. Different 3D printers and related devices may be based on different technologies, such as stereolithography (SLA), digital light processing (DLP), fused deposition modeling (FDM), selective laser sintering (SLS), selective laser melting (SLM), electronic beam melting (EBM), laminated object manufacturing (LOM) and 2-photon polymerization (2PP). These 3D printing processes may be pushed to their limits with other additive/subtractive technologies to realize high-throughput 3D microelectrode arrays 20 as described.

It is possible to use micro selective laser melting (μSLM). This process has been found effective for the fabrication of high density, low throughput 3D printed stainless steel microelectrode arrays. However, this fabrication technique still requires an insulation step during fabrication when manufacturing devices in 3D. In accordance with a non-limiting example, the microelectrode array 20 may be fabricated by a combination of inexpensive polymer 3D printing, which is followed by techniques that add conductive functionalities, thus resulting in self-insulated and high-throughput 3D microelectrode arrays in two steps.

The current microelectrode array 20 as described provides commercial and academic scientists with tools to improve their ability to monitor, control and evaluate electro-active tissue in a high-throughput process. The fabrication process as described is more accurate, productive and cost-effective in scaling up a tool traditionally presented in a single sample analysis format to a high-throughput, ANSI/SLAS-compatible format. The bifacial design that includes the 3D printed well plate 24 having the top face 28 and bottom face 32 includes the 3D self-isolated microelectrodes 54 on the top face and configured in an array (or non-array) within each culture well 36. The conductive traces 50 for electrical connections on the bottom face 32 are added in a second step such as by silver ink casting/printing into the microtroughs 44, and metal casting/printing into the 3D printed, 3D hollow vertical microchannels 40. This eliminates the need for insulation any for microelectrodes 54 and reduces multiple assembly processing steps, thereby saving time and costs.

In a non-limiting example, the microelectrode array 20 may be designed using the Solidworks software platform, e.g., the 2020×64 bit edition, which permits rapid design concepts to be generated. Three design configurations of this high-throughput, multi-well microelectrode array 20 were developed: 1) a 6-well configuration (FIGS. 1A and 1B); 2) a 12-well configuration (FIGS. 10 and 1D); and 3) a 24-well configuration, shown in FIGS. 6A-6D. Each of the culture wells 36 in the 6/12 well 3D printed well plate 24 includes ten (10) 3D printed and self-isolated microelectrodes 54 that had been 3D printed as an array of 3D hollow vertical microchannels 40 and had been subsequently filled with the conductive paste 50, e.g., the silver ink. The bifacial design includes the top face 28 having the 3D self-isolated microelectrodes 54 printed as 3D hollow, vertical microtowers formed as microchannels 40, which in a non-limiting example, have a height of about 600 μm in one embodiment, an outer diameter of about 900 μm, and an inner diameter that is filled with the conductive paste 50 of about 700 μm.

Ink casting may be performed from the bottom face 32, enabling self-insulation. The microtroughs 44 on the bottom face 32 are configured in this example with a width of about 540 μm, and a depth of about 300 μm that permit the ink casting process to form the conductive traces 58. The microtroughs 44 that are filled with the conductive paste 50 may terminate into hollow microreservoirs, which in an example, may have a depth of about 600 μm (not illustrated in detail), which may subsequently serve as contact pads 66. These contact pads 66 may be configured to interface with commercial electronics amplifier systems, e.g., an Axion BioSystems Maestro and AxIS software.

Depending on end use requirements, the 6-well, 12-well and later described 24-well well plate 24, in a non-limiting example, may have an overall length of about 127.8 mm, a width of about 85.5 mm, and a height of about 20.13 mm with a ±3 mm variation to cover most well plate designs. These dimensions may vary, of course, depending on the end use and types of culture wells that are required. Individual culture wells 36 may have an inner diameter and wall thickness and be configured in a cylindrical configuration as illustrated of about 34.6 mm and 1.4 mm (6-well) and about 22.4 mm and 1.4 mm (12-well) respectively. As explained below for the 24-well microelectrode array 20, dimensions may vary and may include a height of about 18.4 mm, an ID of about 16.5 mm, and an OD of about 19.5 mm. Each culture well 36 may include its array (or non-array) of isolated microelectrodes 54.

It should be understood that the microelectrodes 54 may be arranged in any configuration, but an array such as two rows of five microelectrodes as shown in FIG. 3A has been found feasible. The stereolithography file for 3D printing in the examples as described may be printed in FormLabs Form 3, and may be operable with a μSLA 3D printer having a laser wavelength of about 405 nm, using a photopolymer clear resin, such as FLGPCL04 from FormLabs. The X- and Y-printing resolution may be determined by the spot size of the laser, which is about 85 μm in a non-limiting example. The axial resolution in the Z direction may be kept at about 100 μm.

Figure 1H:
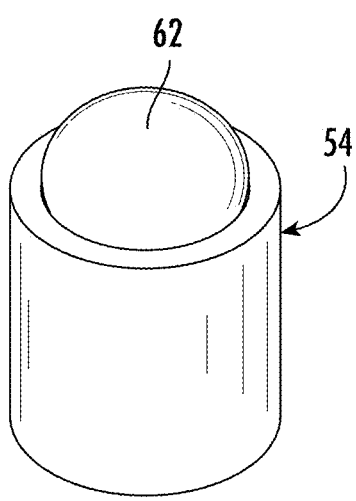
FIG. 1H is an enlarged schematic isometric view of an example microelectrode formed in a culture well with the conductive paste filling the microchannel.
Figure 1I:
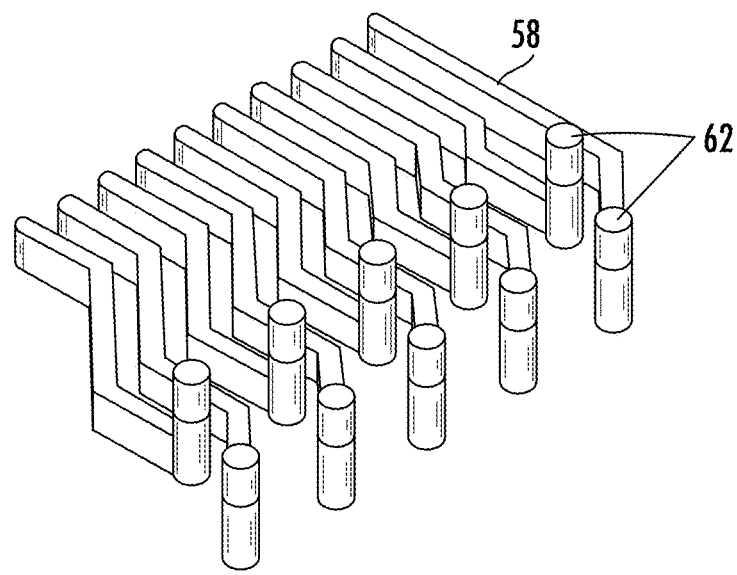
FIG. 1I is a schematic isometric schematic view of the electrical traces and filled vias formed in the bottom face of the 3D printed well plate opposite a culture well.

To obtain an optimized print quality for the various features that constitute the microelectrode array 20, it was printed in one example at 20° with respect to an anchor/substrate holder used with the 3D printing system, but other angles as described below were later used. The 3D printing bifacial configuration having the top face 28 and bottom face 32 allows for ink casting (FIG. 1E) using, for example, Epo-tek® EJ2189 from Epoxy Technologies Inc. on the bottom face of the 3D printed well plate 24 so that the hollow microtowers as the microchannels 40 (FIG. 1F) are filled with the conductive paste along with the microtroughs 44 to form the conductive traces 58 for electrical connections (FIGS. 1F-1I), and forming the completed self-insulated 3D microelectrode array 20 having self-isolated microelectrodes 54 on the top face 28 (FIG. 1H). Impedance spectroscopy was performed using a Bode 100 from Omicron Labs with Dulbecco's Phosphate Buffer Solution such as from Thermo Fisher Scientific, Waltham, Mass., US, as the electrolyte. The collected data cluster was imported into a MATLAB® (MathWorks) and Origin Software software program for processing and analysis.

Referring now to FIGS. 2A and 2B, there are shown images of the monolithically 3D printed 6-well high-throughput 3D microelectrode array 20 showing the top and bottom faces 28,32 respectively. Referring now to FIGS. 2C and 2D, there are shown images of the monolithically 3D printed 12-well high-throughput 3D microelectrode array configuration showing the top and bottom faces 28,32 respectively. The silver ink as the conductive paste 50 in this example selectively fills the 3D printed microtroughs 44 on the bottom face 32 to form the conductive traces 58 and the microchannels as the microtowers 40 on the top face 28 to form the microelectrodes 54.

Referring now to FIGS. 2E and 2F, there are shown photomicrographs of a single culture well 36 in the 6- and 12-well configuration respectively. The images show the patterned and self-isolated 3D isolated microelectrodes 54 on the top face 28 and the conductive traces 58 on the bottom face 32 of the 3D printed microelectrode array 20. The images additionally depict the monolithic construction with features such as the culture well 36, and contact pads 66, and the structure may include alignment features as explained in greater detail below.

Figure 3B:
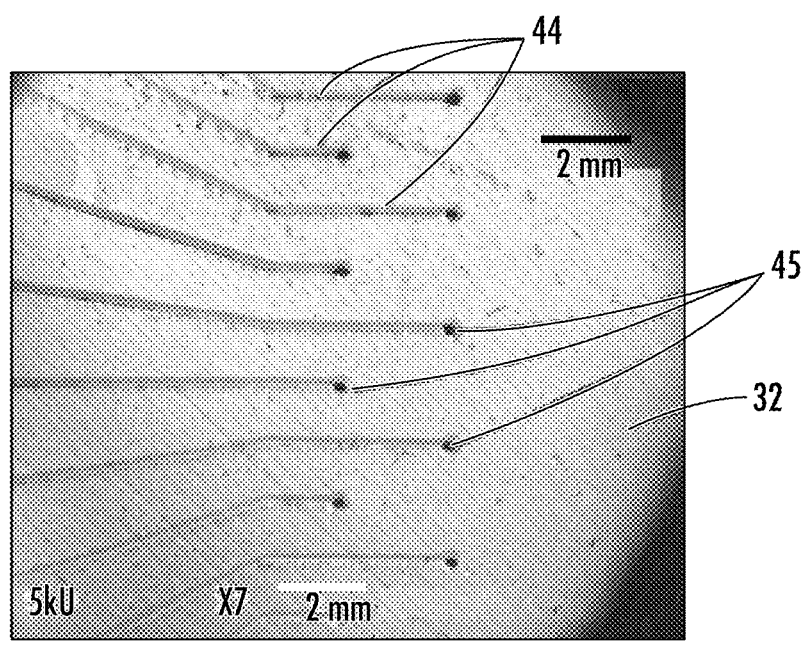
FIG. 3B is a SEM image of 3D printed microtroughs opposite the culture well of FIG. 3A and configured for selective ink casting on the bottom face of the 3D printed well plate.
Figure 3C:
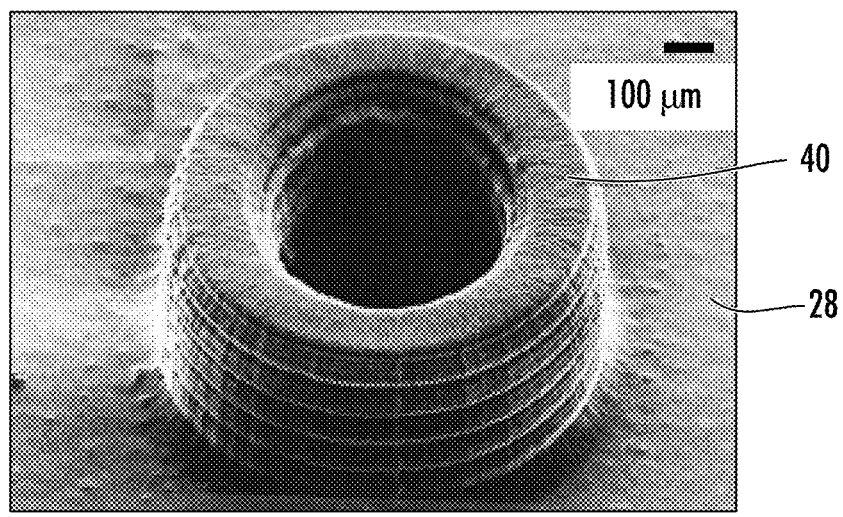
FIG. 3C is a SEM image of an unfilled single microchannel on the top face within a culture well.
Figure 3D:
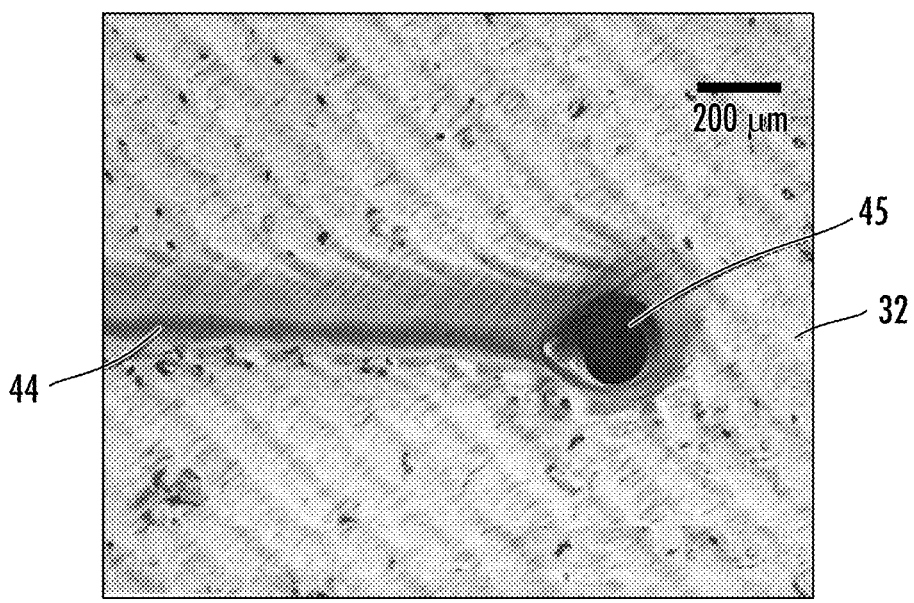
FIG. 3D is a SEM image of an unfilled microtrough on the bottom face of the 3D printed well plate and showing the orifice leading to the microchannel for communication thereof.

FIGS. 3A and 3B are SEM images of a single culture well 36 looking towards the respective top and bottom faces 28,32 respectively, and showing the 3D printed microchannels 40 and microtroughs 44. The close-up micrographs of FIGS. 3C and 3D show a 3D hollow, vertical microchannel 40 (FIG. 3C) that has not yet been filled with the conductive paste 50 and a single microtrough 44 (FIG. 3D) showing its end having the via or orifice 45. This excellent design-to-device transition to form the microelectrode array 20 may be achieved using the selective ink casting process. The actual inside diameter of the 3D hollow, vertical printed microchannels 40 in an example are smaller than the design parameters with actual dimensions of about 600 μm±30 μm (N=10), and the design diameter of about 700 μm. The height of the 3D, hollow vertical microchannels 40 in an example are about 600 μm±5 μm (N=10), with the design parameters being about 600 μm.

Figure 3E:
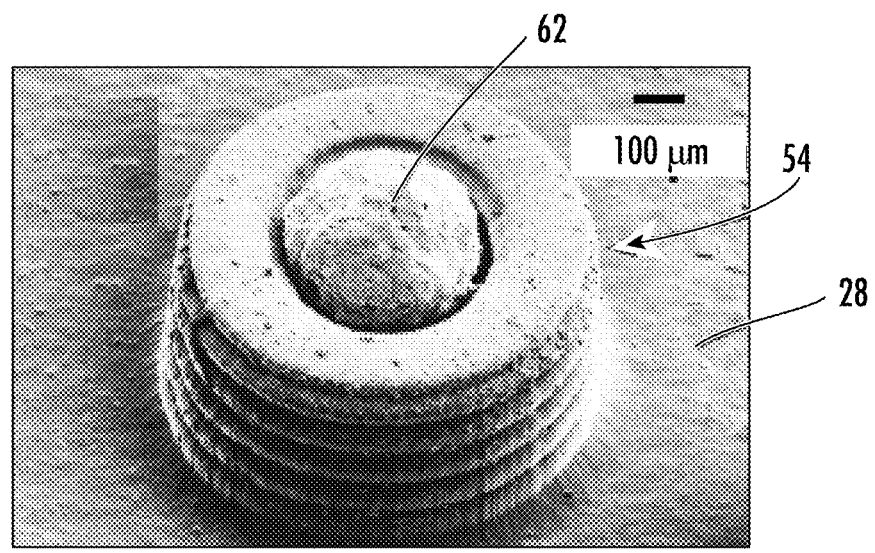
FIG. 3E is a SEM image of a microelectrode after the microtrough is filled with the conductive paste.

Referring to FIG. 3E, there is shown a SEM image illustrating the hollow 3D printed microchannel 40 post-ink casting looking from the top face 28, which when filled with the ink or other conductive paste 50, forms the self-isolated microelectrode 54 once the ink, i.e., conductive paste 50 has filled the structure.

Figure 3F:
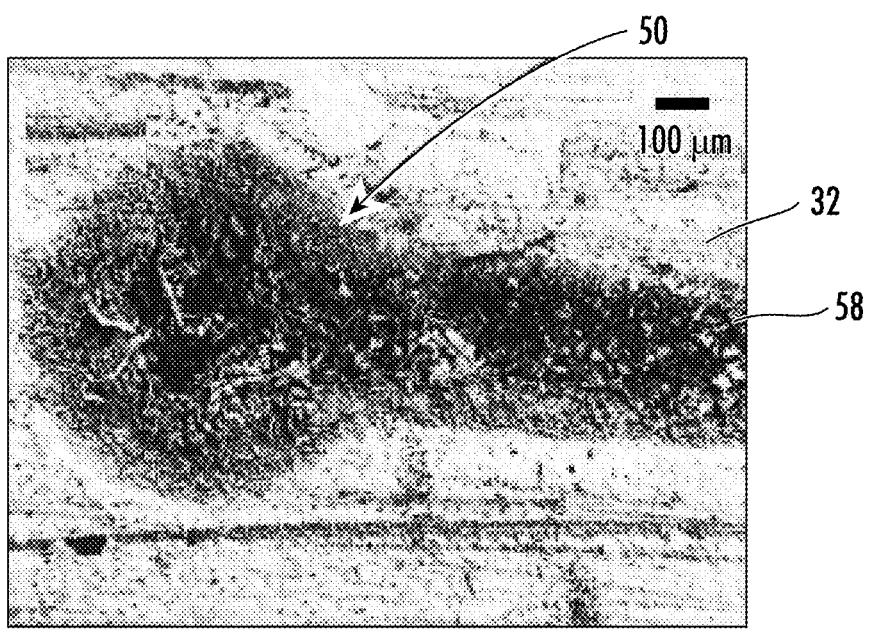
FIG. 3F is a SEM image showing a conductive trace on the bottom face after selective ink casting the microtroughs.

Referring to FIG. 3F, there is shown a SEM image of the bottom face 32 of the completed 3D microelectrode array 20 in which the microtrough 44 has been filled or ink cast with silver conductive ink or paste 50 to form the conductive trace 58 and contact pad 66. After ink casting from the bottom face 32 in an example, a desired, high top surface area as a finished "mushroom shaped" and/or microbullet, enlarged top contact section 62 of the microelectrode 54 is formed on the top section of the microchannel 40 as best shown in FIGS. 1H and 3E. The radius of curvature of this "mushroom" and/or microbullet as the top contact section 62 as shown in the enlarged image of FIG. 1H and the SEM image at FIG. 3E is about 208 μm in a non-limiting example. Additionally, the "mushroom" and/or microbullet shaped top contact section 62 of the microelectrode 54 makes an obtuse angle of about 135° with the top of the microchannel 40.

Figure 5A:
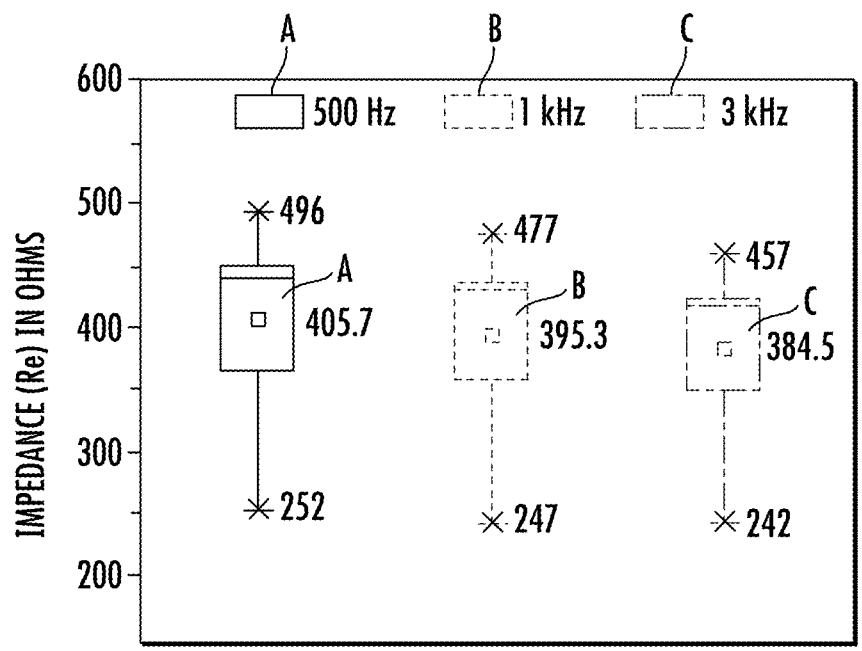
FIG. 5A is a histogram chart showing the impedance well-to-well variation for three electrodes for M=3 microelectrodes for C=6 culture wells (M×C=18 total).
Figure 5B:
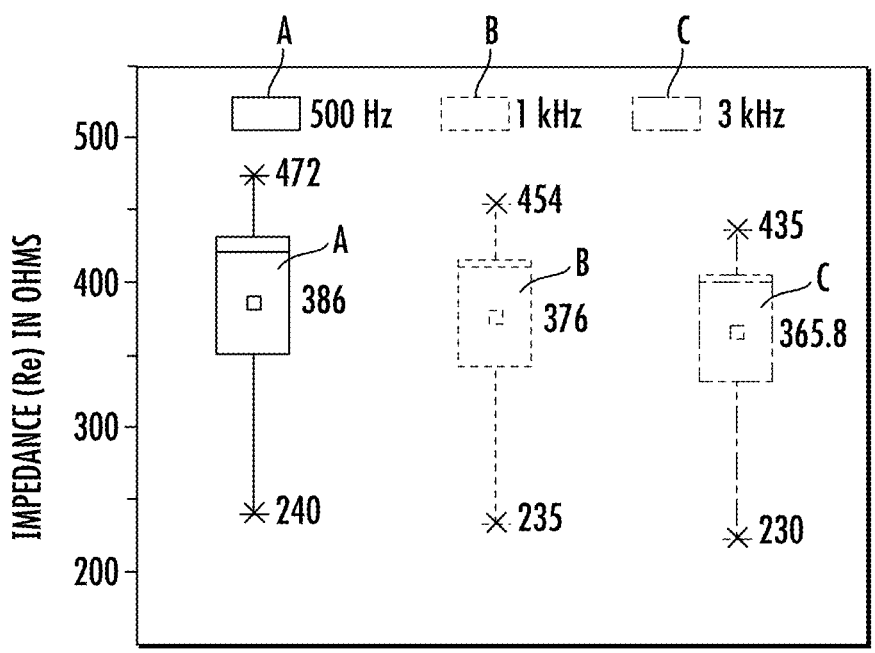
FIG. 5B is a histogram chart for the impedance well-to-well variation for M=3 microelectrodes for C=12 culture wells (M×C=36) total.

Referring now to FIG. 4, there is a graph showing the impedance in ohms on the left vertical axis, the phase in degrees on the right vertical axis, and the frequency on the horizontal axis. The average full spectrum impedance as the real part and the phase as the imaginary part for N=10 microelectrodes 40 for both the 6-well and 12-well microelectrode arrays 20 across several culture wells 36 depict ideal microelectrode behavior. Further analysis on the consistency of impedance is shown in the graphs of FIGS. 5A and 5B, which show the impedance in ohms at 500 Hz, 1 KHz, and 3 KHz for the well-to-well variations in the 6-well and 12-well 3D printed well plate configurations respectively. Those listed electrophysiologically relevant frequencies may pertain to cardiac/neural applications and correspond to the 500 Hz, 1 kHz, and 3 kHz frequencies. These values remain in close tolerance for M=3 electrodes for C=6 wells for M×C=18 total, and for M=3 electrodes for C=12 wells for M×C=36 total, for the 6-well and 12-well 3D printed well plate 24.

From the graphs, it is seen that that the mean of the real part of the impedance varies by only 4.9%, 4.8% and 4.9% at the 500 Hz, 1 kHz, and 3 kHz frequencies among the 6-well and 12-well configuration. This evidence shows the excellent reproducibility of the fabrication process. The diameter of the culture wells 36 may vary as noted before, and in an example, includes about 5 to about 15 microelectrodes per culture well, but may preferably include between about 2 and 64 microelectrodes, and in another example, up to 1,000 microelectrodes.

As the culture well 36 count has increased, it has been found that the printing angle and device orientation has an effect on the 3D printing fabrication of these high-throughput (HT), self-isolated, 3D printed 3D microelectrode arrays 20 for in vitro biotechnology applications. Makerspace based development using micro-Stereolithography (μSLA) 3D printing and ink casting techniques has increased efficiency and in an example developed a 24-well microelectrode array 20 (FIGS. 6A-6D) with self-isolated 3D microelectrodes 54 having 100% yield, and in an example, seven microtowers per well 36, acting as supports for the microelectrodes 54. This 24-well microelectrode array 20 configuration as shown in FIGS. 6A-6D was analyzed by Optical Microscopy, Electrical Impedance Spectroscopy (EIS), Laser Scanning Confocal Microscopy, and Scanning Electron Microscopy, and the process optimization results were interpreted using established μSLA theory, which allows for greater understanding of the process relationships for these high-throughput, 3D printed 3D microelectrode arrays. These studies permitted further scalability, denser electrodes, and higher culture well 36 counts for high-throughput screening in biotechnology.

As the number of culture well 36 counts increased, fill factors increased for the resulting microelectrode arrays 20, and the micro-Stereolithography (μSLA) 3D printing process was optimized as a combination of multiple variables: lateral (X, Y) and vertical (Z) print resolutions, support structure placement, device orientation with respect to a substrate holder, printing angle, laser power (P), maximum exposure energy (Emax) and critical energy (Ec), feature distances, and other variables. Some of these parameters were predefined in the μSLA 3D printer used to make the microelectrode arrays 20, but other parameters were manipulated in order to optimize the final printing and microelectrode array characteristics. Some techniques optimized the printing process using a simulation of sensitive parameters, such as temperature and photo initiator properties, and increased the degrees of freedom in the ultraviolet source and substrate.

The manufacture of the 24-well microelectrode array 20 as a bioplate having seven microelectrodes 54 per culture well 36 with self-isolated microelectrodes 54 was optimized. Testing and characterization of the 24-well microelectrode arrays 20 as bioplates after variation in the printing angle and device orientation with respect to the base plane significantly improved the isolation of the conductive traces 58 and was supported by the correlation between numerical and experimental findings. It was determined that the need for any mechanical or chemical post-processing steps for finishing the surfaces of the microelectrode array 20 was reduced. With these results, the 3D printing process may be scaled to higher density, high-throughput 3D microelectrode arrays 20 by optimizing the different processing and manufacturing variables as discussed further below.

Optimizing 3D printing is considered by some skilled in the art as a process of maximization. For example, having a maximum number of parallel or perpendicular faces with respect to a base plane, and referenced as a horizontal plane created by the resin surface, during a μSLA 3D printing process, for example, may increase the surface quality, and thus, minimize the stepping phenomena created by devices as the microelectrode array 20 that are oriented using various tilt angles. Using this criteria, four different printing angles with respect to the base plane (0°, 12°, 20° and 24°) were evaluated.

A Stepping Line-Width Artifact (SLWA) phenomenon was tracked and defined during these observations in both the vertical microchannel or microtower 40 vias or openings 45 and microtrough 44 definition. Some increase in the SLWA was found in tilted versions of the printed structure forming the microelectrode array 20.

During the ink casting step, the conductive silver ink was defined in the microtroughs 44 and unintended connected conductive traces 58, and hence, shorting may result. From initial theory, the 0° tilt printed version was expected to not have SLWA due to the maximization on the number of parallel and perpendicular surfaces due to its orientation. A flat and smooth surface on the conductive traces 58 side and no short circuits were expected in the 3D printing along with full 3D definition of the microtowers as the vertical microchannels 40.

In order to overcome the trace-shorting expected at various tilt angles, 3D printed surfaces due to SLWA, an additional step could be performed as was known to those skilled in the art to minimize the short circuit, i.e., employing fine mechanical sanding over the surface, or acetone polishing. This additional step was eliminated with the optimization process as developed and described below aiding in manufacturing efficiency.

The 24-well high-throughput, 3D microelectrode array 20 was designed in this example using Solidworks 2020 CAD software (Dassault Systemes) as shown in the example of FIGS. 6A-6D using ANSI/SLAS standards with overall dimensions (L×W×H): about 127.8 mm×85.5 mm×20 mm. The device as the microelectrode array 20 was 3D printed at 0°, 12° and 24° tilt angle using a Form 3 printer (FormLabs) and rapid prototyping resin Clear v4 FLGPCL04, having the support structures placed on the culture wells, top side looking towards the top face 28. One additional version was printed at a 20° tilt angle with the support structures on the conductive traces/back side as the wells-side orientation.

In this example, a total of 168 isolated 3D microelectrodes 54, i.e., seven per well, were designed. The 3D microelectrodes 54 were formed from the microtowers as the microchannels 40 with open ports or vias 45 and having the following dimensions: about 800 μm height, 1000 μm outer diameter (OD) and 800 μm inner diameter (ID). These microtowers 40 were connected to individual microtroughs 44 that formed the conductive traces 58 on the backside of the microelectrode array 20 and in an example dimensioned (L×D): about 400 μm×400 μm, and forming 3D microelectrodes 54 upon metallization/ink casting.

The μSLA process used a laser wavelength of about 405 nm at 250 mW power, and a 85 μm laser spot size in a non-limiting example. Print resolutions for the various printed configurations were maintained at Z (100 μm) and X/Y resolution (25 μm). A bottom-up printing process was used, although other similar 3D printing processes may be used. The devices as the microelectrode arrays 20 were immersed twice in Isopropyl Alcohol (IPA) (Sigma-Aldrich) for 15 minutes and air dried for 30 minutes. A final UV curing step (at about 405 nm) for 15 minutes at about 60° C. was performed to enhance the mechanical strength and robustness of the structure forming the microelectrode array 20. Optical characterization of the resultant high-throughput, 3D microelectrode array 20 structure was performed using a Stereoscope (SMZ800, Nikon), to obtain more precise information about the definition of the microtowers 40 that formed the microelectrode 54 and conductive traces and microtroughs.

Trace metallization for the conductive traces 58 and microelectrodes 54 was performed using an ink casting technique with two silver conductive pastes 50: 1) Silver Paste EP3HTSMED (Masterbond), and 2) Prima-Solder EG8050 (AI Technology). Both conductive pastes 50 were cured at about 60° C. for about 20 hours to obtain full strength. Further end-to-end, e.g., from the backside at the bottom face 32 to the top face 28 of the 3D microelectrode array 20 on the front, resistance measurements were performed using a Source Meter Mod. 2400 (Keithley, Tektronix). Gold electroplating on top of the defined silver 3D microelectrodes 54 as the top contact section 62 in an example was made using Sulfite Gold Plating Solution TSG-250 (Transene Company) and a Platinum (Pt) counter electrode with a 50% AC cycle square pulse of amplitude 1 A/cm2 for 30 s.

Electrical Impedance Spectroscopy (EIS) was performed using a Vector Network Analyzer (Bode 100, Omicron Lab) with Phosphate Buffer Solution (PBS) as an electrolyte and Pt/Ti wire as a counter electrode. The collected data was post processed using Origin software (OriginLab) for statistical and impedance/phase analysis during frequency sweeping in the range of 1-10 MHz. High precision imaging was performed using Scanning Electron Microscopy (SEM, TM3000, Hitachi) and Laser Scanning Confocal Microscope (VK-X1000, Keyence) in order to characterize the stepping effect, shape, dimensions and profile.

Figure 6A:
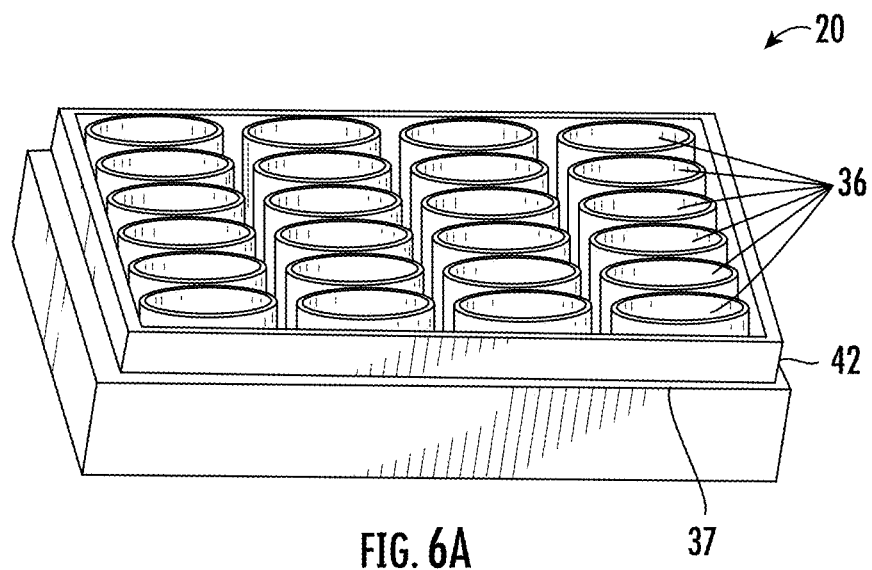
FIG. 6A is an isometric view looking toward the top face of a 24-well 3D microelectrode array.
Figure 6B:
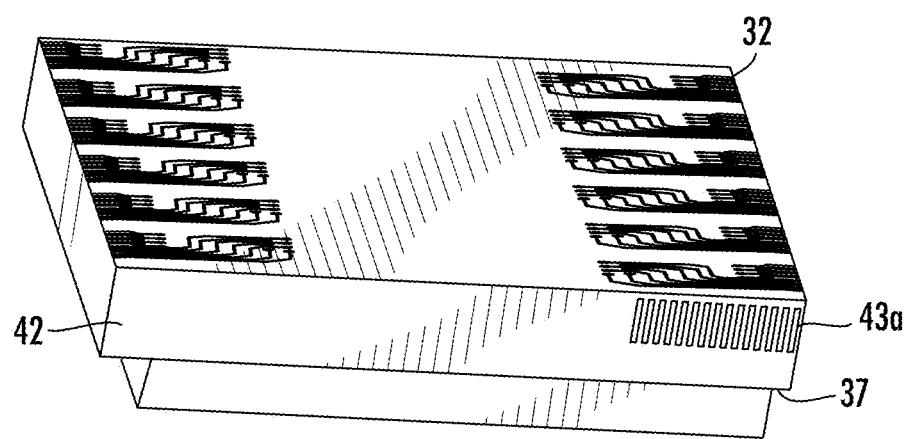
FIG. 6B is an isometric view looking toward the bottom face of the 3D microelectrode array of FIG. 6A.
Figure 6C:
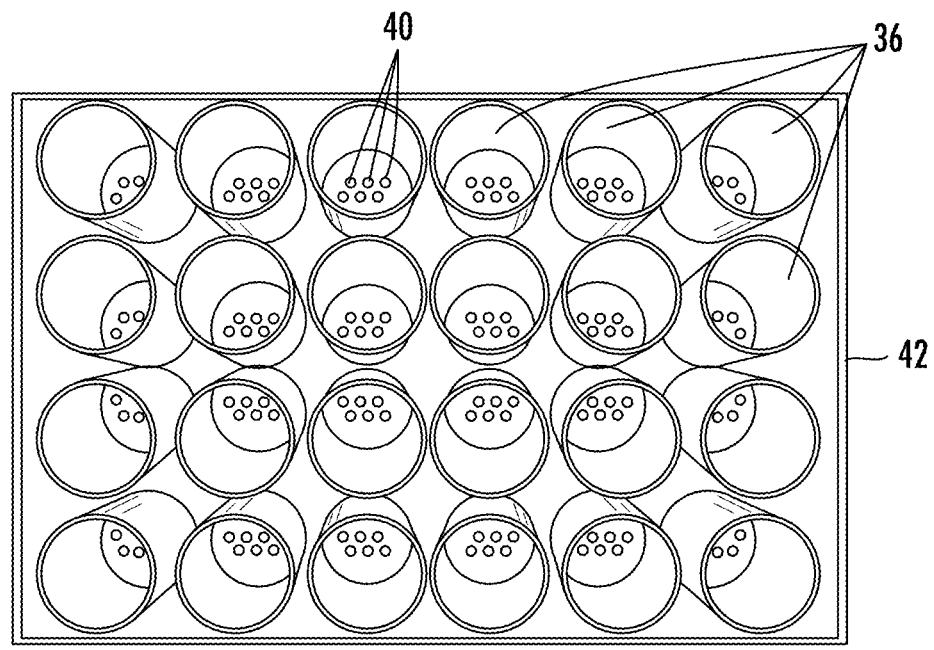
FIG. 6C is an optical image looking toward the top face of the 3D microelectrode array of FIG. 6A.
Figure 6D:
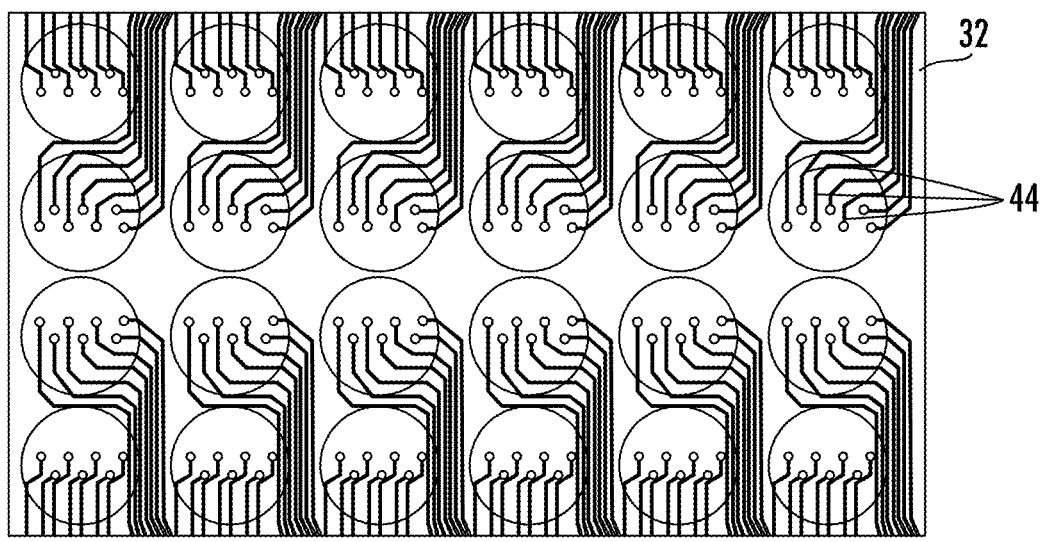
FIG. 6D is an optical image looking toward the bottom face of the 24-well 3D microelectrode array of FIG. 6A.
Figure 6E:
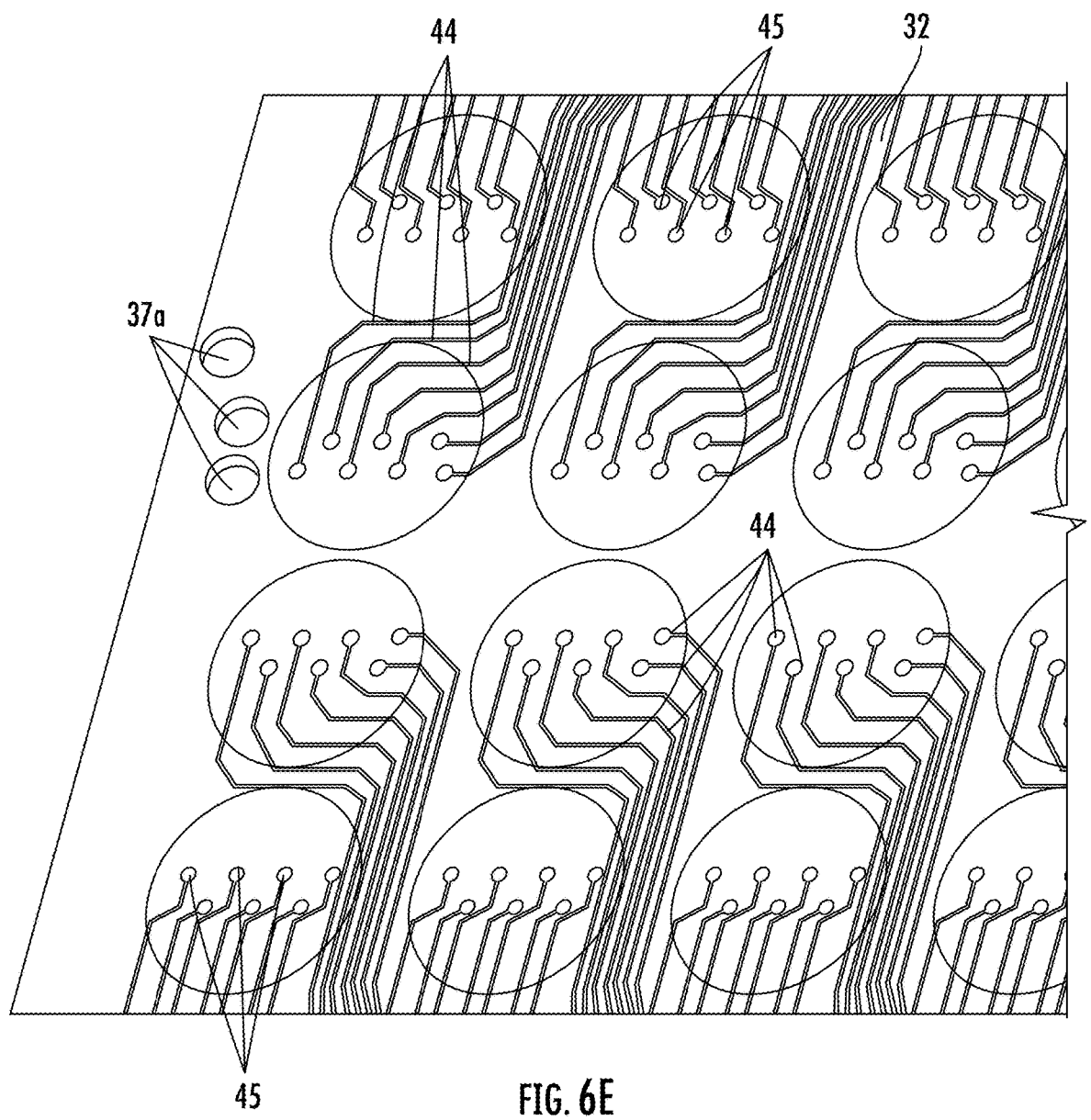
FIG. 6E is an enlarged optical image of the 3D microelectrode array of FIG. 6D showing in greater detail the microtroughs and vias formed at the bottom face.
Figure 6F:
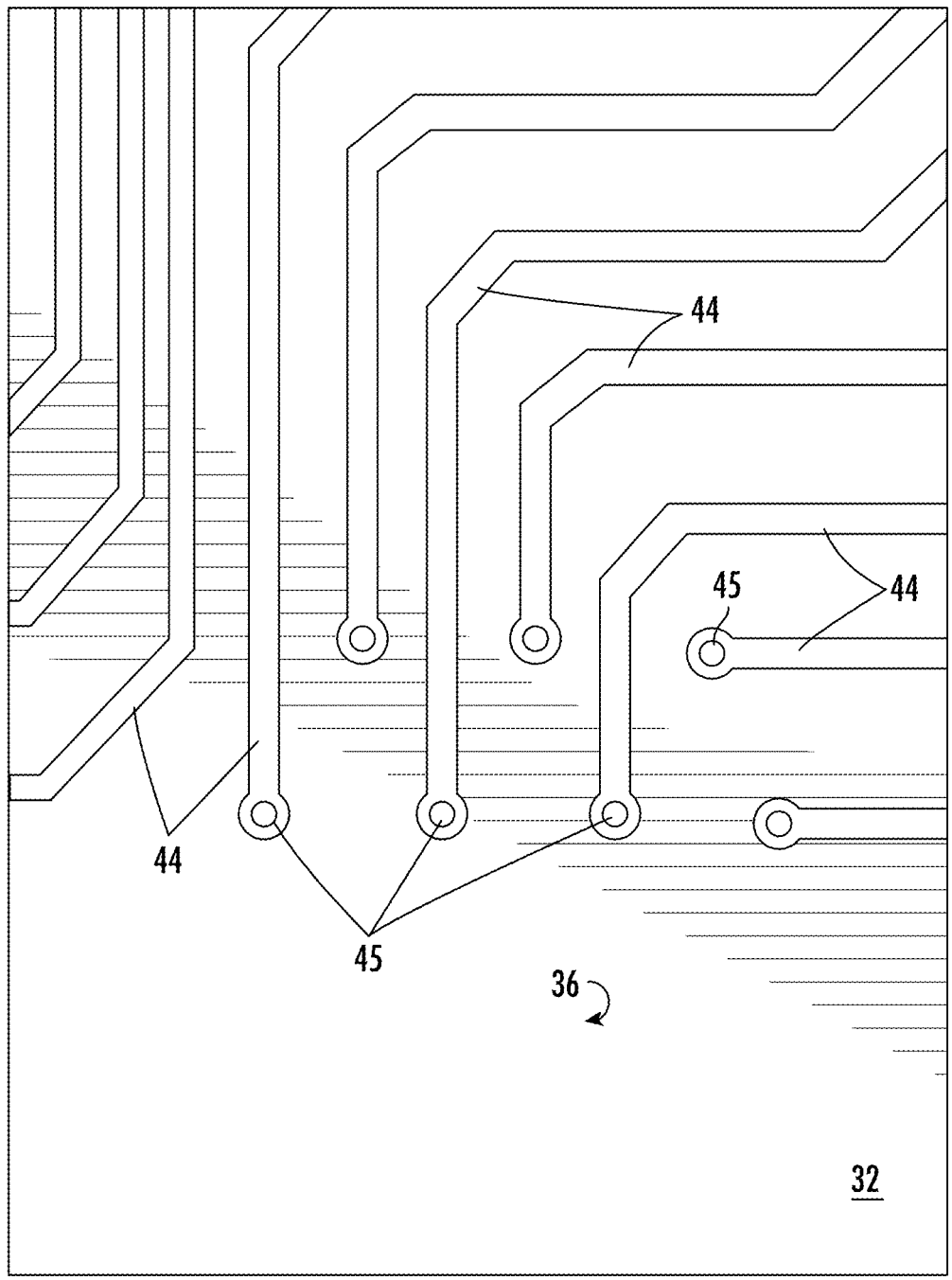
FIG. 6F is an enlarged optical image of the 3D microelectrode array of FIG. 6E showing greater detail of the microtroughs and vias formed at the bottom face at one culture well location.
Figure 6G:
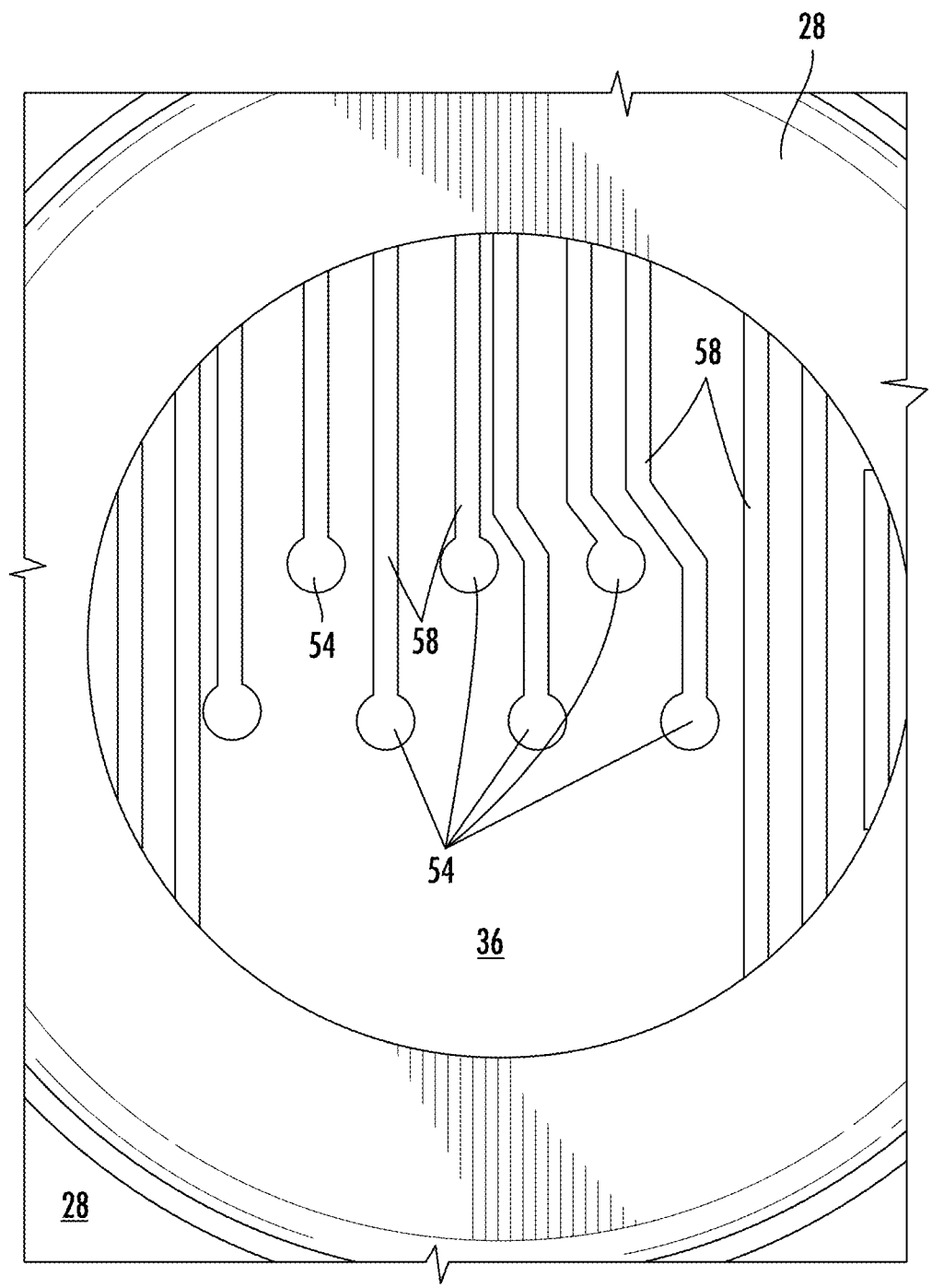
FIG. 6G is an enlarged optical image of a single culture well showing the microtroughs and vias filled with conductive paste to form self-isolated microelectrodes and the conductive traces visible through the clear resin.

Table I presents a summary of the different 3D printing conditions used for the high-throughput, microelectrode arrays 20 and basic observations on the percentage of open microchannels as microtowers 40 and microtroughs 44 that formed the conductive traces 58 after preliminary optical observations under a stereoscope.

configuration shown in FIGS. 6A and 6B show a stepped configuration with a step 37 or ledge, and in FIG. 6B showing schematically by an example of the three holes in FIG. 6E on the middle left side, one or more alignment features 37a, which allow alignment. The alignment features 37a can be different configurations as grooves, slots, holes, or other features to aid in alignment for end-use microelectrode array uses, such as vertical grooves shown at 43a in FIG. 6B. FIGS. 6C and 6D are optical images. The images of FIGS. 6E and 6F are enlarged views and show a number of culture wells 36 from the bottom face 32 view and the microtroughs 44 and vias 45, which are shown in greater detail of the enlarged view of a single culture well in FIG. 6F. Another view looking from the top face 28 down into a single culture well 36 and showing the microelectrodes 54 and conductive traces 58.

Figure 7A:
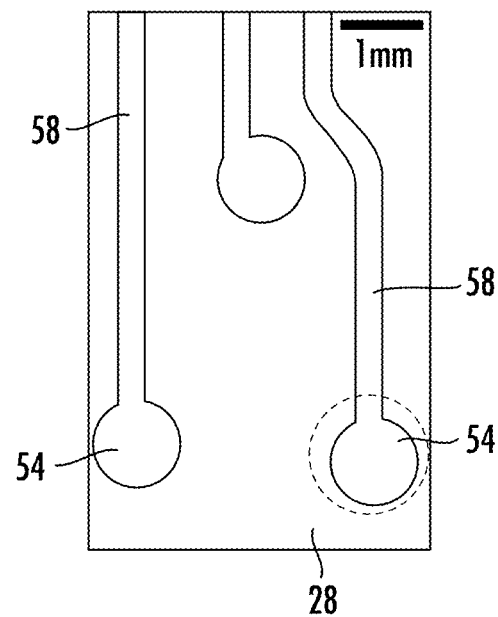
FIG. 7A is an enlarged optical confocal image of a single culture well of the 3D microelectrode array from the top view and showing three microelectrodes.
Figure 7B:
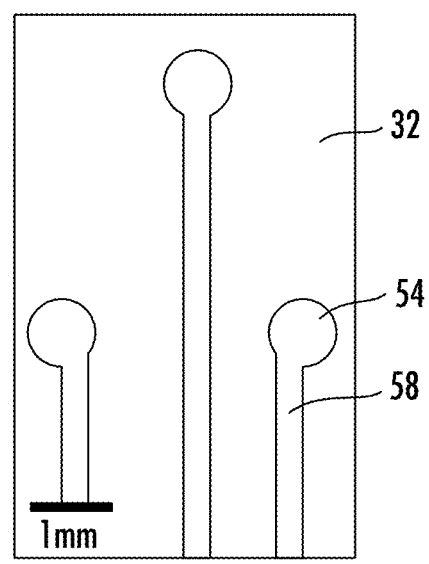
FIG. 7B is an optical confocal image of the single well of FIG. 7A looking from the bottom and showing the conductive traces.
Figure 7C:
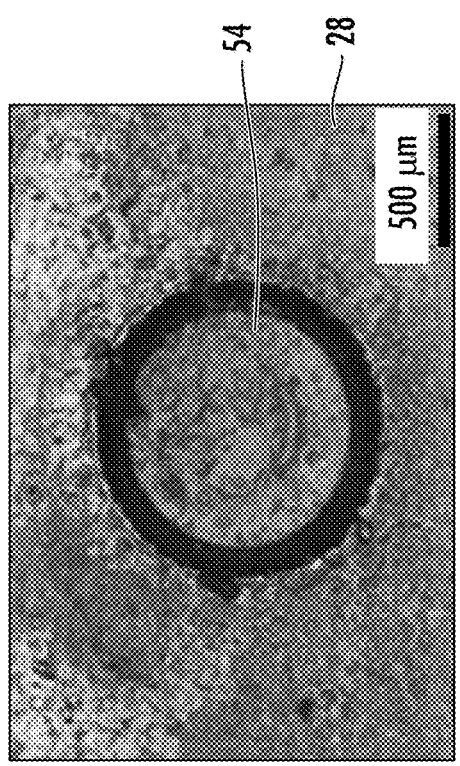
FIGS. 7C-7F are laser confocal images of a microelectrode in 3D profile and top view of the filled (FIGS. 7C and 7D) and unfilled (FIGS. 7E and 7F) microelectrode.
Figure 7D:
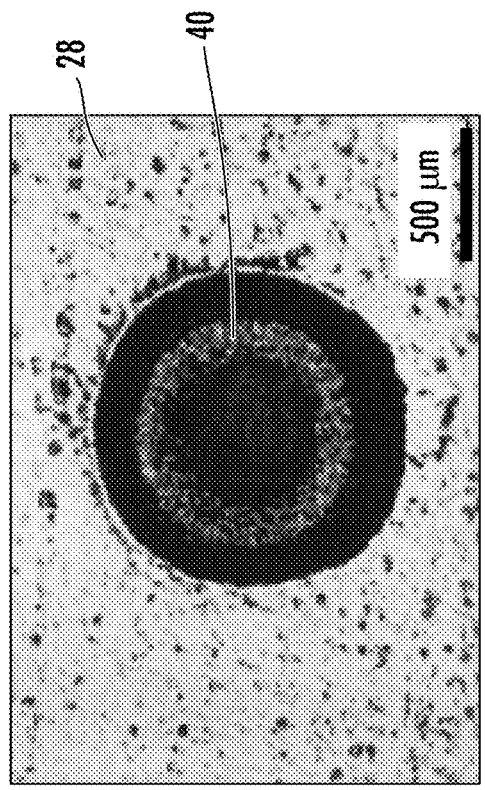
Figure 7E:
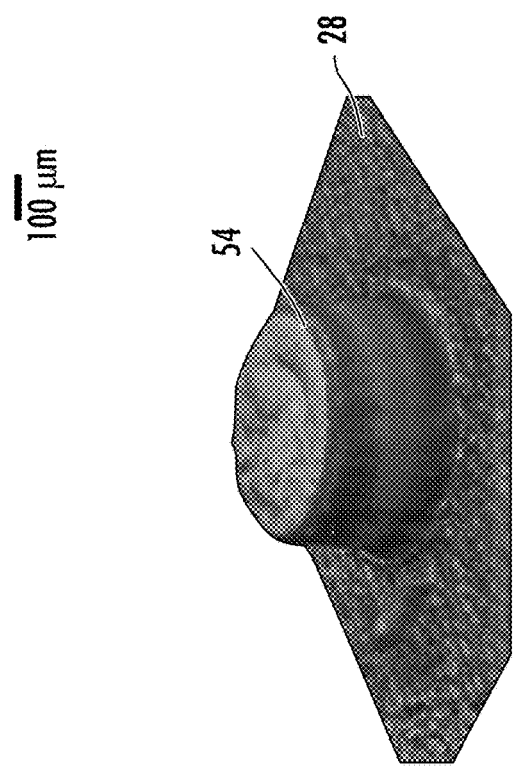
Figure 7F:
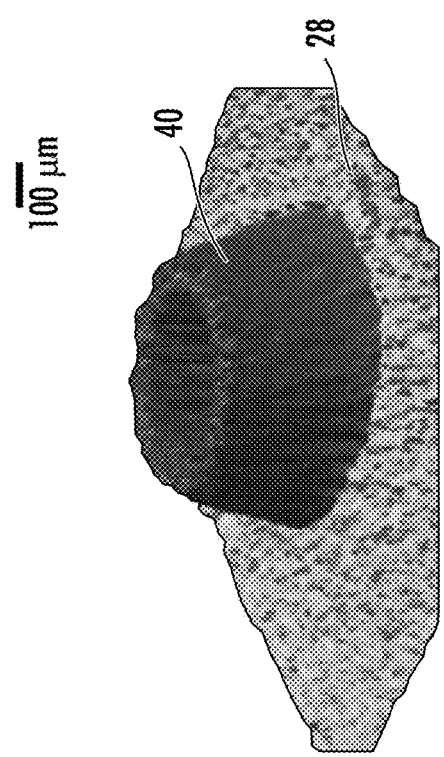

FIGS. 7A and 7B depict optical microimages of the 0° tile angle and the ink casting of the defined 3D microelectrodes 54 and conductive traces 58 at two orientations, i.e., wells-side looking down towards the top face 28 (FIG. 7A) and with an example microelectrode 54 shown by the dotted circle, and the traces-side looking down towards the bottom face 32 (FIG. 7B). FIGS. 7C to 7F show laser scanning confocal microscopic 3D images (FIGS. 7C and 7E) and corresponding optical images (FIGS. 7D and 7F) of respective filled (FIGS. 7C, 7D) and unfilled (FIGS. 7E, 7F) vias 45 forming the microelectrodes 54 as shown I FIGS. 7C and 7D in the high-throughput microelectrode array 20 that was printed at 0° tilt angle. There did not appear to be any trace of SLWA on the conductive traces 58 as may have been predicted by theory, and the completely isolated conductive traces did not require further processing. The 3D microelectrodes 54 are well defined and may have the mushroom shaped top contact section 62 that may benefit 3D organoid stimulation applications.

TABLE I

Process Conditions and General Characterization for All the 3D Printed Microelectrode Arrays

| Orientation (Tilt Angle °) | Support Structures Orientation (Attachment) | Open Microtowers (%) | Open Traces (%) | Printed Resin Volume (mL) | Printed Layers (n) | Printing Time (min) | 3D printing post-processing (conditions) |
|---|---|---|---|---|---|---|---|
| 0° | Topside/Wells | 100 | 100 | 62.26 | 270 | 465 | IPA Bath x2 15 min each |
| 12° | Topside/Wells | 98.2 | 100 | 76.46 | 439 | 585 | min each |
| 20° | Bottomside/Traces | 100 | 50.6 | 64.48 | 543 | 570 | Air Drying 30 min |
| 24° | Topside/Wells | 27.4 | 100 | 58.34 | 591 | 540 | UV Curing @ 60° C. 15 min |

The best results were obtained at a tilt angle of 0° for all the metrics measured. The microtowers 40 that later form the microelectrodes 54 were fully open for a 20° tilt angle but the orientation, support structures and SLWA reduced the conductive traces 58 definition efficiency down to about 50% for 85 out of 168, necessitating additional post-processing. The 12° tilt angle orientation resulted in comparable performance to the 0° tilt angle 3D printing, however, that 3D printing at the 12° tilt angle suffered in the print volume, number of layers, and other measures. The 24° orientation resulted in the worst definition of the 3D microtower 40 structures with only 27.4% of the microtowers that would later form the 3D microelectrodes 54 being fully open.

Figure 8A:
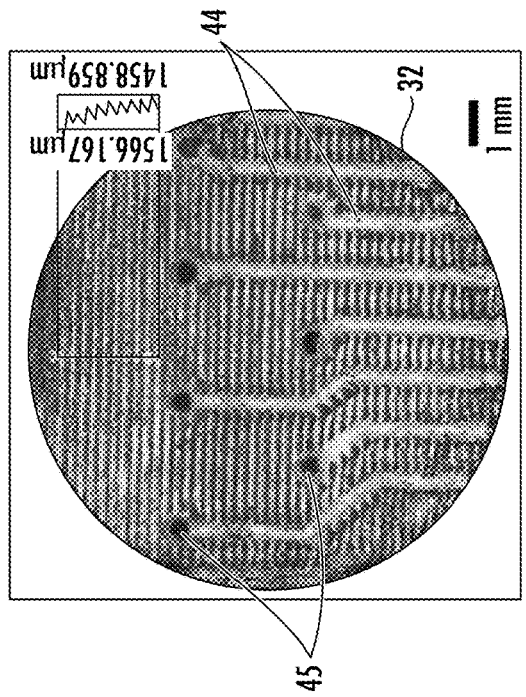
FIG. 8A is an isometric view of a 24° tilt angle 3D printed version of the conductive traces at a single culture well.
Figure 8B:
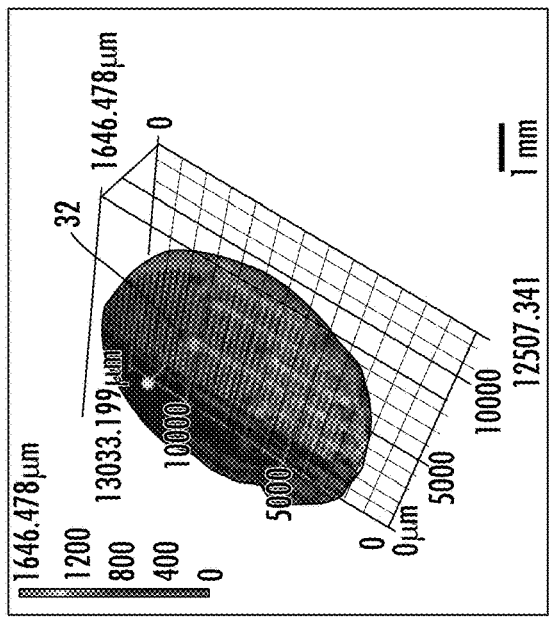
FIG. 8B is a top view of the conductive traces and Traces and Stepping Line-Width Artifact (SLWA) shown in FIG. 8A.
Figure 8C:
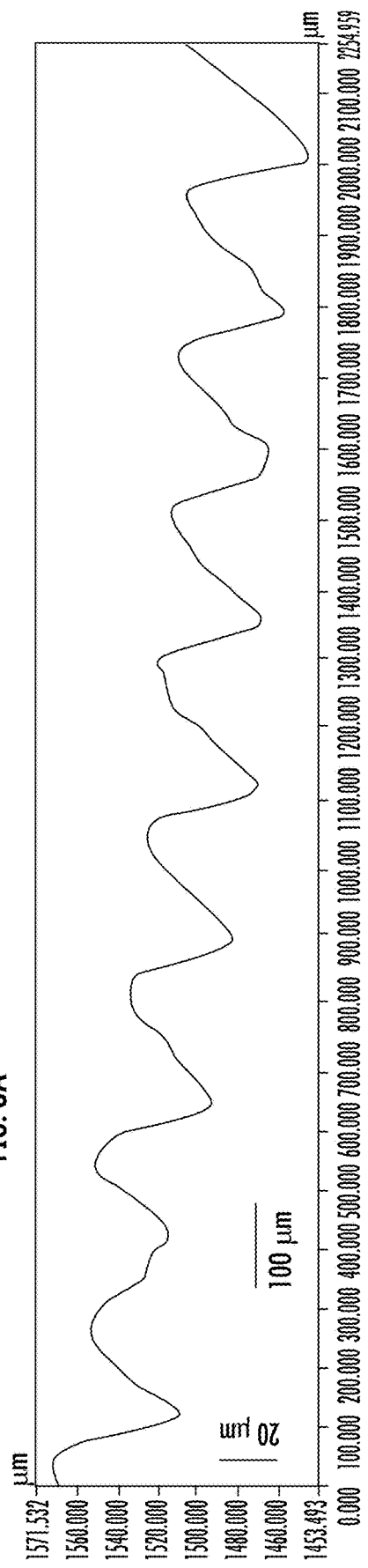
FIG. 8C is a graph showing a scaled profile of the SLWA denoting a triangular shaped curve with the Y-axis at a 20 μm scale and the X-axis at a 100 μm scale.
Figure 9:
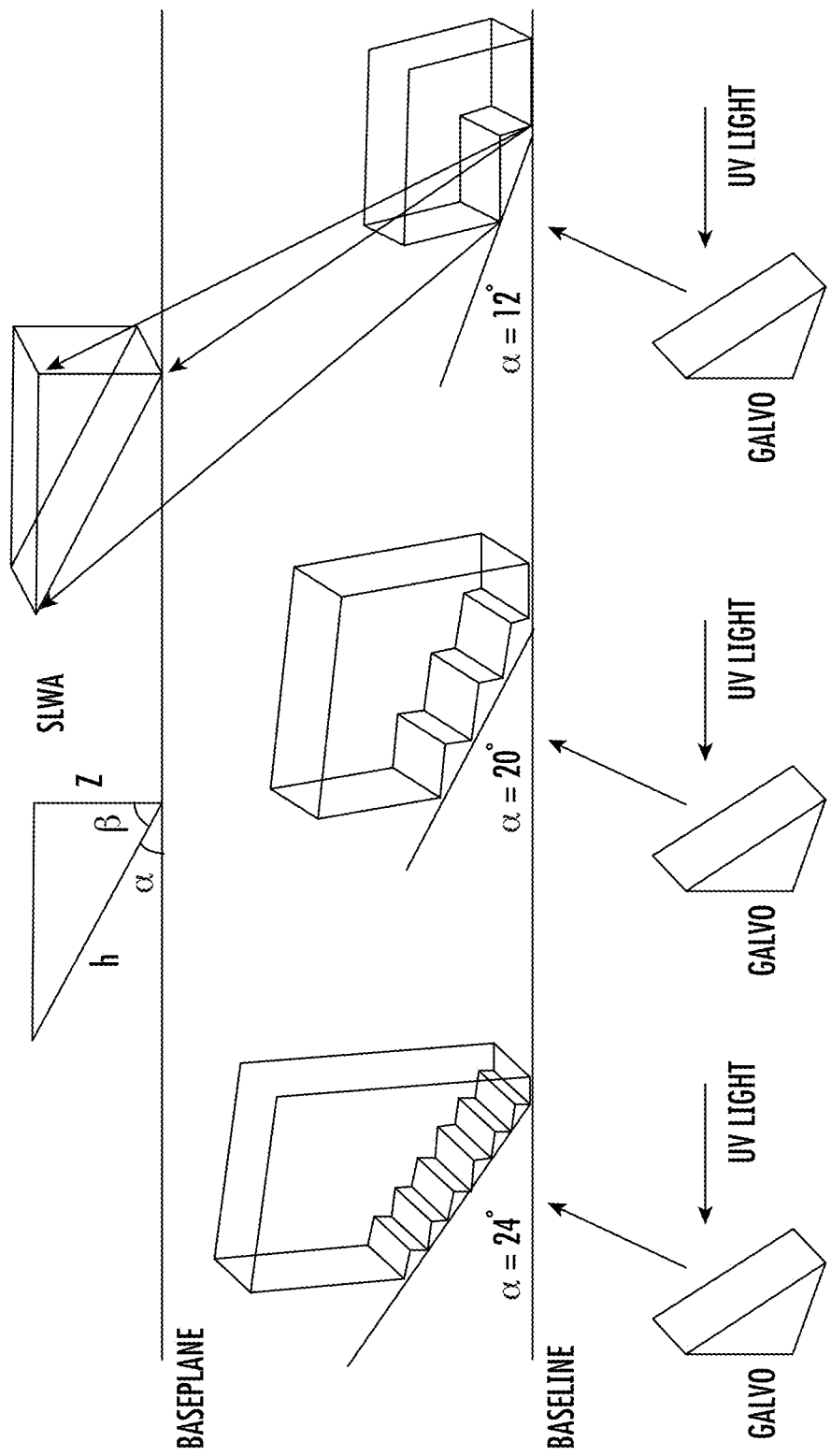
FIG. 9 is a schematic, isometric diagram showing the Stepping Line-Width Artifact of the 3D printing.
Figure 10A:
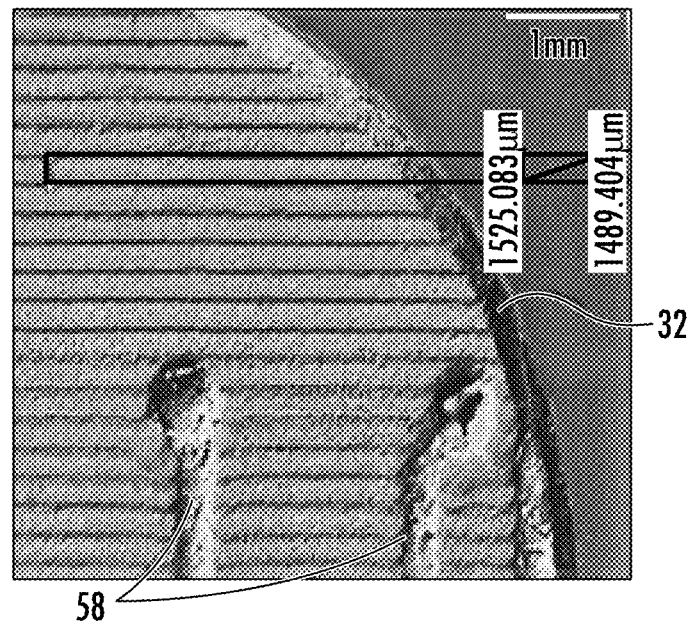
FIGS. 10A and 10B are images of a portion of conductive traces and SLWA in the 24° tilt angle 3D printed version.
Figure 10B:
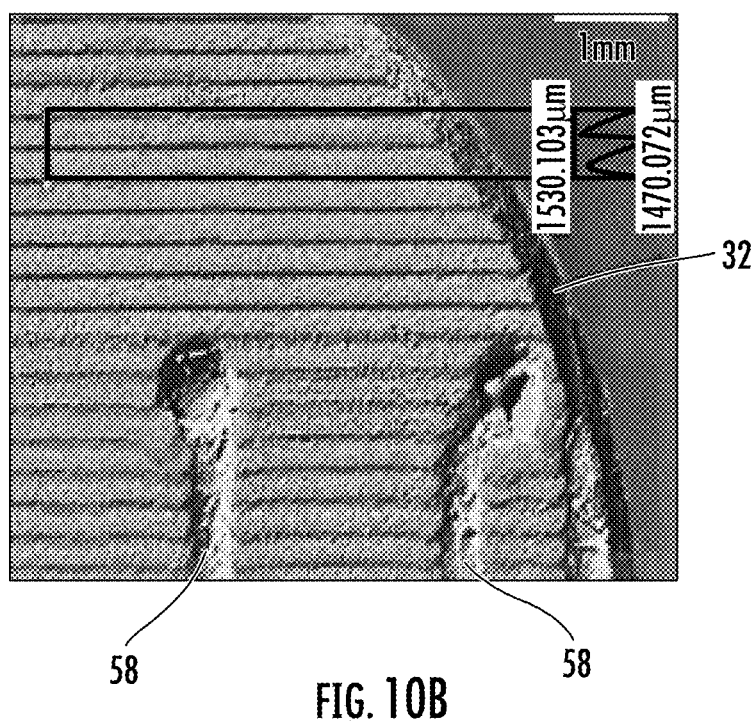
Figure 10C:
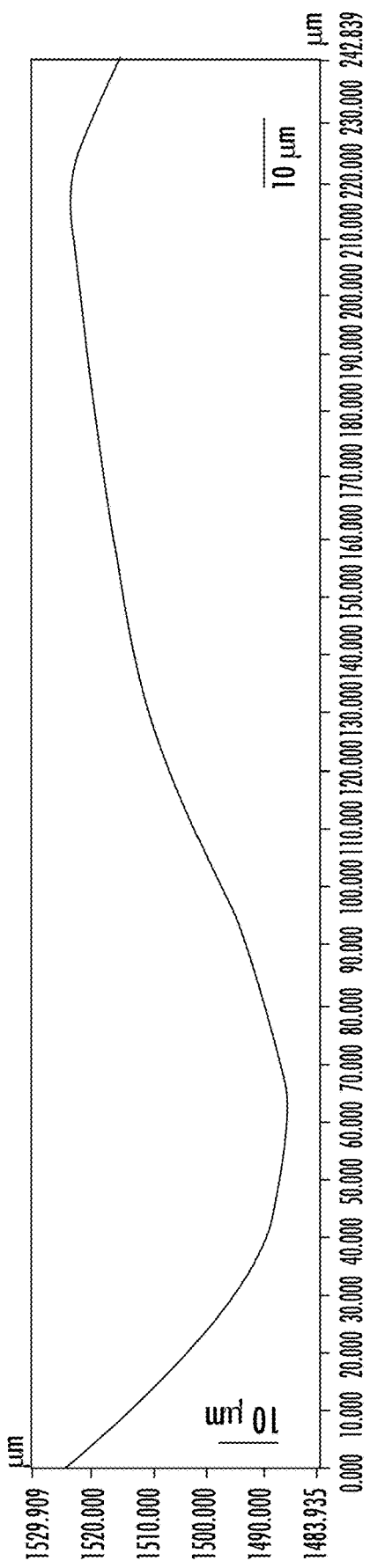
FIGS. 10C and 10D are the respective graphs that profile the images of FIGS. 10A and 10B with the scales in FIG. 10C having at the X-axis: 10 μm and Y-axis: 10 μm, and for FIG. 10D the X-axis: 20 μm and Y-axis: 10 μm.
Figure 10D:
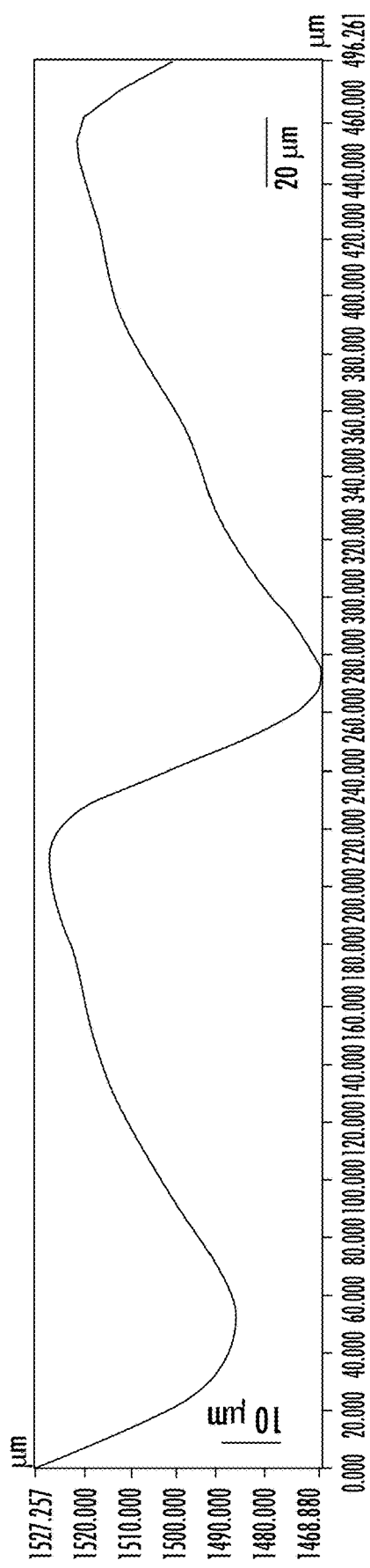

Referring again to FIGS. 6A-6D, an example of a 24-well microelectrode array 20. The outer peripheral well 36 in the Laser confocal microscope images are shown in the 3D isometric view looking towards the bottom face 32 of FIG. 8A, and plan view looking down towards the bottom face in FIG. 8B, and depicting the profile images using laser confocal microscope for the 24° tilt 3D printing of the microelectrode array 20 and having lateral profiling. The tilt angle may range, however from 0° to 90°. The tilt angle may be based upon the orientation of a support surface against the top or bottom faces during 3D printing. The printing angle and orientation may be changed to optimize printing and isolation of the well plate, conductive traces, and microchannels. A scaled profile of the SLWA showing a triangular shaped curve is illustrated in the graph of FIG. 8C with the Y-axis at 20 μm scale and the X-axis at the 100 μm scale. Derivation of this SLWA can be performed by applying geometric calculations using the 3D printing process for inclination and orientation as shown in the geometric configurations depicted in the drawing of FIG. 9, indicating the stepping effect and line width artifact with the SLWA denoted as "h" inherent to SLA 3D printing, and showing the SLWA in the top row, the base plane in the second row with the different tilt angles.

This calculation depicts the wider SLWA for increased inclinations of 3D printing, thus creating uneven surfaces and unintended short-circuits among microtroughs 44 and resulting conductive traces 58 in the 24-well high-throughput 3D microelectrode arrays 20. These calculations reveal the relationships between the angles and SLWA distances may be provided by the equations below:

$$\alpha+\beta=90°$$

$$\beta=90°-\alpha \quad (1), \text{ and}$$

$$h=z/\cos(\beta) \quad (2),$$

where "$\alpha$" is the angle of tilt in 3D printing and "z" is the vertical resolution of the 3D printer. The variable of interest is "h," which is the mathematical representation of SLWA. Theoretically, h increases when lowering the inclination angle, and for 0° becomes infinite giving a smooth printed surface defined by the parallel face optimization.

Theoretical "h" can be calculated as 246 µm (tilt angle: about 24°; z resolution: about 100 µm). These values correlate with the experimental dimensions presented in the graphs of FIGS. 10A-10D, with SEM images in FIGS. 10A and 10B, and calculated SLWAs represented by profiles in the graphs shown in FIGS. 10C and 10D (220 µm and 235 µm). Differences from theory can be attributed to changes in the actual 3D printed resolution in the "z" resolution due to energy-dependent curing. These experimental results for SLWA in the 24° tilt angle 3D printed version are shown in these images of FIGS. 10A and 10B with the selection of one and two SLWA on the traces-side looking down at the bottom face 32 and their profiling depicted in the graphs for FIGS. 10C and 10D respectively, with scales for FIG. 10C: X-axis: 10 µm, Y-axis:10 µm, and the scales for FIG. 10D: X-axis: 20 µm, Y-axis: 10 µm.

SEM images and measurements of the microelectrode array 20 are presented in the images of FIGS. 11A and 11B that demonstrate the surface flatness observed in the high-throughput, 3D microelectrode array 20 printed at 0° tilt angle showing in FIG. 11A unfilled microtroughs 44 and the filled conductive traces 58 in FIG. 11B. The relatively smooth surface observed due to a SLWA value of infinity as calculated theoretically correlated to printing an optimized surface. On the other hand, for tilted versions as presented in the images of FIGS. 12A and 12B, appreciable SLWA is observed and this becomes an undesirable feature and showing the microtroughs 44.

The SEM images of the microelectrode array 20 on the traces-side at different inclination angles show the Stepping Line-Width Artifact where the 24° tilt device and orientation are shown with support structures on wells-side looking down at the top face 28 (FIG. 12A), and the 20° tilt device and orientation with support structures on traces-side looking down at the bottom face 32 (FIG. 12B) are shown.

Figure 13:
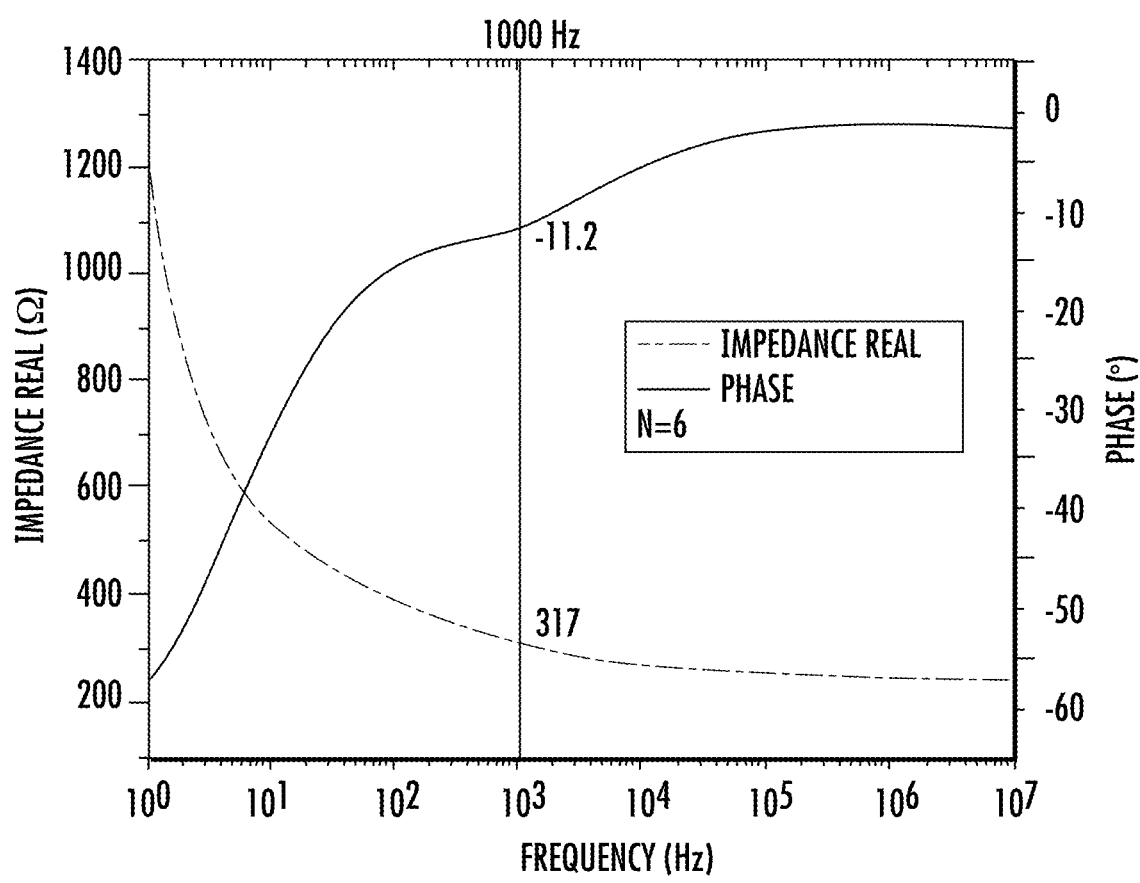
FIG. 13 is a graph showing the impedance and phase signature for data representing an average N=6 gold 3D microelectrodes from a single well on the 24-well microelectrode array of FIGS. 6A-6D.

The graph of FIG. 13 shows the impedance and phase signature for gold 3D microelectrodes with an average of N=6, from a single well on the 24-well high-throughput microelectrode array printed at 0° tilt angle.

Figure 14A:
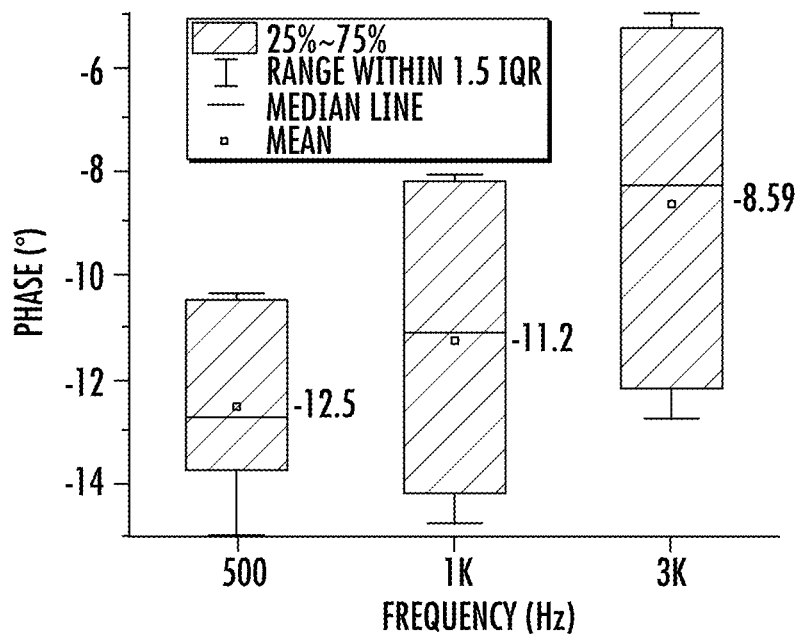
FIG. 14A is a histogram showing phase versus frequency in a non-limiting example for the 24-well microelectrode array.
Figure 14B:
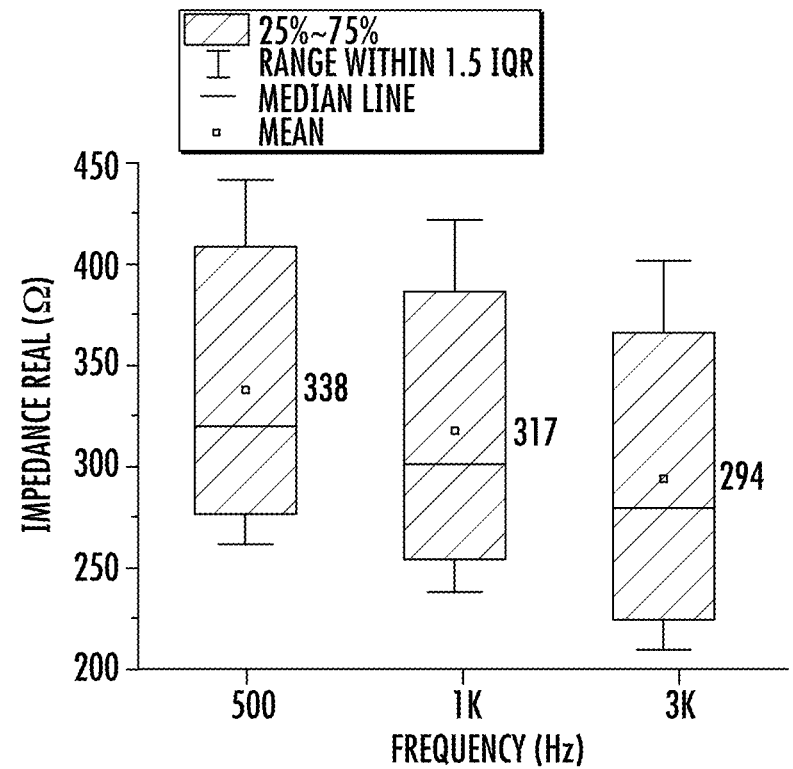
FIG. 14B is a histogram showing the impedance versus frequency for the 24-well microelectrode array.

This averaged (N=6) end-to-end microelectrodes 54 resistance for 0° tilt angle printed version was 0.41Ω (Ohms). As noted above, the graph of FIG. 13 shows the full spectrum impedance averaged for N=6 gold plated electrodes in the optimized version printed at a tilt angle of 0°. The curves depict the desired microelectrode 54 behavior for biological applications with mean values of 317Ω (Ohms) and −11.2° (Degrees) at the electrophysiological relevant frequency of 1 kHz. The histogram of FIG. 14A illustrates the phase versus frequency, and the histogram of FIG. 14B illustrates the impedance versus frequency.

It is evident that the tilt angle and device orientation have an effect on the µSLA 3D printing of complex structures for the high-throughput microelectrode arrays 20 as described. Minimization of the remnant line width artifact inherent to the µSLA process was best shown at the 0° tilt, wells-side (looking down at the top face 28) oriented design.

This application is related to copending patent application entitled, "3D PRINTED, HIGH-THROUGHPUT MICROELECTRODE ARRAY," which is filed on the same date and by the same assignee and inventors, the disclosure which is hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method of forming a high-throughput, three-dimensional (3D) microelectrode array for in vitro electrophysiological applications, comprising:
   3D printing a well plate having a top face, a bottom face and a plurality of culture wells on the top face, and each culture well including a plurality of 3D printed, vertical microchannels on the top face, and microtroughs on the bottom face communicating with the microchannels, wherein the well plate and the plurality of culture wells are 3D printed onto a support structure that is positioned such that 3D printing occurs from the culture wells upward to the well plate using a bottom-up 3D printing process at a 0 to 12 degree orientation tilt angle relative to the well plate as a base plane; and
   filling the microtroughs and the microchannels with a conductive paste to form self-isolated microelectrodes in each culture well and conductive traces that communicate with the self-isolated microelectrodes.

2. The method of claim 1 wherein each microelectrode includes a contact formed at a top section of the microchannel.

3. The method of claim 1 wherein the conductive traces terminate into contact pads configured to interface with an electrophysiological circuit component.

4. The method of claim 1 wherein each culture well includes about 2 to about 64 microelectrodes.

5. The method of claim 1 comprising 3D printing a photopolymer clear resin.

6. The method of claim 1 comprising 3D printing an outer peripheral wall extending from the top face.

7. The method of claim 1 wherein the microelectrodes are arranged in an ordered or random array within each culture well.

8. The method of claim 1 comprising 3D printing one or more alignment features in the well plate.

9. The method of claim 1 comprising varying a printing angle and an orientation with respect to the base plane to optimize printing and isolation of the well plate, the conductive traces, and the microchannels.

10. A method of forming a high-throughput, three-dimensional (3D) microelectrode array for in vitro electrophysiological applications, comprising: 3D printing a well plate having a top face and a bottom face; forming on the top face a plurality of culture wells, wherein each culture well includes a plurality of 3D printed, vertical microchannels on the top face, and microtroughs on the bottom face communicating with the microchannels, wherein the well plate and the plurality of culture wells are 3D printed onto the support structure that is positioned such that 3D printing occurs from the culture wells upward to the well plate using a bottom-up 3D printing process at a 0 to 12 degree orientation tilt angle relative to the well plate as a base plane; ultraviolet curing the 3D printed well plate, the culture wells, the microchannels and the microtroughs; and filling the microtroughs and the microchannels with a conductive paste to form self-isolated microelectrodes in each culture well and conductive traces that communicate with the self-isolated microelectrodes.

11. The method of claim 10 wherein each microelectrode includes a contact formed at a top section of the microchannel.

12. The method of claim 10 wherein the conductive traces terminate into contact pads configured to interface with an electrophysiological circuit component.

13. The method of claim 10 wherein each culture well includes about 2 to about 64 microelectrodes.

14. The method of claim 10 comprising 3D printing a photopolymer clear resin.

15. The method of claim 10 comprising 3D printing an outer peripheral wall extending from the top face.

16. The method of claim 10 wherein the microelectrodes are arranged in an ordered or random array within each culture well.

17. The method of claim 10 comprising 3D printing one or more alignment features in the well plate.

18. A method of forming a high-throughput, three-dimensional (3D) microelectrode array for in vitro electrophysiological applications, comprising: forming by 3D printing a well plate having a top face, a bottom face, and a plurality of culture wells on the top face; and each culture well including a plurality of 3D printed, vertical microchannels on the top face, and microtroughs on the bottom face communicating with the microchannels, wherein the well plate and the plurality of culture wells are 3D printed onto a support structure that is positioned such that 3D printing occurs from the culture wells upward to the well plate using a bottom-up 3D printing process at a 0 to 12 degree orientation tilt angle relative to the well plate as a base plane; ultraviolet curing the 3D printed well plate, the culture wells, the microchannels and the microtroughs; and filling the microtroughs and the microchannels with a conductive paste to form self-isolated microelectrodes in each culture well and conductive traces that communicate with the self-isolated microelectrodes, each of said self-isolated microelectrodes having an electroplated top surface.

19. The method of claim 18 comprising cleaning and air drying the 3D printed well plate, the culture wells, the microchannels and the microtroughs.

20. The method of claim 18 wherein the conductive traces terminate into contact pads configured to interface with an electrophysiological circuit component.

21. The method of claim 18 wherein each culture well includes about 2 to about 64 microelectrodes.

22. The method of claim 18 comprising 3D printing a photopolymer clear resin.

23. The method of claim 18 comprising 3D printing an outer peripheral wall extending from the top face.

24. The method of claim 18 wherein the vertical microchannels are arranged in an ordered or random array within each culture well.

* * * * *